(12) United States Patent
Frinking et al.

(10) Patent No.: US 9,307,957 B2
(45) Date of Patent: Apr. 12, 2016

(54) AUTO-SCALING OF PARAMETRIC IMAGES

(75) Inventors: Peter Frinking, Manno (CH); Marcel Arditi, Manno (CH); Laurent Mercier, Manno (CH); Nicolas Rognin, Manno (CH); Eric Allemann, Manno (CH)

(73) Assignee: BRACCO SUISSE SA, Manno (CH)

( * ) Notice: Subject to any disclaimer, the term of this patent is extended or adjusted under 35 U.S.C. 154(b) by 478 days.

(21) Appl. No.: 13/377,143

(22) PCT Filed: Jun. 8, 2010

(86) PCT No.: PCT/EP2010/058031
§ 371 (c)(1),
(2), (4) Date: Dec. 8, 2011

(87) PCT Pub. No.: WO2010/142694
PCT Pub. Date: Dec. 16, 2010

(65) Prior Publication Data
US 2012/0082359 A1  Apr. 5, 2012

(30) Foreign Application Priority Data

Jun. 8, 2009 (EP) .................... 09162171

(51) Int. Cl.
| | |
|---|---|
| *G06K 9/00* | (2006.01) |
| *A61B 8/08* | (2006.01) |
| *A61B 8/06* | (2006.01) |
| *G06T 5/00* | (2006.01) |
| *G06T 5/40* | (2006.01) |
| *A61B 5/00* | (2006.01) |
| *A61B 6/00* | (2006.01) |

(52) U.S. Cl.
CPC .............. *A61B 8/5215* (2013.01); *A61B 8/06* (2013.01); *A61B 8/481* (2013.01); *G06T 5/009* (2013.01); *G06T 5/40* (2013.01); *A61B 5/72* (2013.01); *A61B 6/5211* (2013.01); *G06T 2207/10132* (2013.01)

(58) Field of Classification Search
None
See application file for complete search history.

(56) References Cited

U.S. PATENT DOCUMENTS

| | | | | |
|---|---|---|---|---|
| 2007/0232909 | A1* | 10/2007 | Hughes et al. | ............. 600/437 |
| 2007/0279500 | A1 | 12/2007 | Castorina et al. | |
| 2011/0188722 | A1* | 8/2011 | Huang | ......................... 382/131 |

FOREIGN PATENT DOCUMENTS

| | | |
|---|---|---|
| CN | 101160097 A | 4/2008 |
| EP | 0458745 | 11/1991 |

(Continued)

OTHER PUBLICATIONS

Jeong Kon Kim et al. "Wash-In Rate on the Basis of Dynamic Contrast-Enhanced MRI: Usefulness for Prostate Cancer Detection and Localization," Journal of Magnetic Resonance Imaging, Sep. 30, 2005, 8 pages.*

(Continued)

*Primary Examiner* — Atiba O Fitzpatrick
*Assistant Examiner* — Ryan P Potts
(74) *Attorney, Agent, or Firm* — Fogg & Powers LLC

(57) ABSTRACT

A data-processing method includes providing a parametric map including a plurality of parameter values, each one characterizing a corresponding location of a body-part. The method includes determining at least one statistical indicator of at least one distribution of a plurality of analysis parameter values corresponding to selected analysis locations, each statistical indicator being indicative of a condition of an analysis region of the body-part defined by the analysis locations.

25 Claims, 22 Drawing Sheets

(56) References Cited

FOREIGN PATENT DOCUMENTS

| EP | 0554213 | 8/1993 |
|---|---|---|
| EP | 08169794.8 | 11/2008 |
| JP | 2003325518 | 11/2003 |
| JP | 2006325746 | 12/2006 |
| JP | 2008073338 | 4/2008 |
| WO | 9115244 | 4/1991 |
| WO | 9409829 | 10/1993 |
| WO | 9516467 | 12/1994 |
| WO | 2008136201 | 11/2008 |

OTHER PUBLICATIONS

Jurgen J. Futterer et al. "Prostate Cancer Localization with Dynamic Contrast-enhanced MR Imaging and Proton MR Spectroscopic Imaging," Radiology: vol. 241: No. 2, Nov. 2006, 10 pages.*

Chinese Office Action issued for Chinese Patent Application No. 201080025290.5; titled: "Auto-Scaling of Parametric Images"; Applicant: Bracco Suisse SA; issued at State Intellectual Property Office of the People's Republic of China on Sep. 2, 2013, China, 29 pages.

Wang Bingjian et al. "Self-adaptive Contrast Enhancement Algorithm for Infrared Images based on Plateau Histogram", Acta Photonica Sinica, vol. 34, No. 2; Feb. 28, 2005, China Academic Journal Electronic Publishing House, Beijing, China; http://www.cnki.net; 3 pages.

International Search report for International Application No. PCT/EP2010/058031, European Patent Office, Nov. 29, 2010, pp. 5.

J. Zhang, W. Hu, Y. Wu, D. Klemer, A. Hall, C. Kahn, "A Novel Model for Contrast Enhanced Ultrasound Video and Its Applications", 2006 IEEE Ultrasonics Symposium, Oct. 2006, IEEE, pp. 1726-1729 (XP031076639).

Andreas Arnold-Bos, Jean-Philippe Mulkasse, Gilles Kervern, "Towards a Model-Free Denoising of Underwater Optical Images", Oceans—Europe 2005, vol. 1, Jun. 20, 2005, pp. 527-532.

Fisher B et al, "Contrast Stretching", Histogram Equalization, Internet Citation, 1994, XP002291289, retrieved from internet: http://www.cee.hw.ac.uk/hipr/html/stretch.html.

Christian Greis, "Technology overview: SonoVue (Bracco, Milan)", European Radiology Supplements, Springer, Berlin, DE, vol. 14, No. 8, Oct. 1, 2004, pp. P11-P15.

Po-Hsiang Tsui and Chien-Cheng Chang, "Imaging Local Scatterer Concentrations by the Nakagami Statistical Model", Ultrasound in Medicine and Biology, New York, NY, US, vol. 33, No. 4, Mar. 27, 2007, pp. 608-619.

Japanese Office Action issued for Japanese Patent Application No. 2012-514452; Applicant: Bracco Suisse SA; issued at Japan Patent Office on Jan. 7, 2014, Japan, 3 pages.

Zhang J. et al: "A Novel Model for Contrast Enhanced Ultrasound Video and Its Applications", Ultrasonics Symposium, IEEE, Vancouver BC, Oct. 2-6, 2006, pp. 1726-1729.

* cited by examiner

US 9,307,957 B2

AUTO-SCALING OF PARAMETRIC IMAGES

PRIORITY CLAIM

The present application is a national phase application filed pursuant to 35 USC §371 of International Patent Application Serial No. PCT/EP2010/058031, filed Jun. 8, 2010; which further claims the benefit of European Patent Application 09162171.4 filed Jun. 8, 2009; all of the foregoing applications are incorporated herein by reference in their entireties.

TECHNICAL FIELD

An embodiment relates to the field of medical equipment. More specifically, an embodiment relates to the analysis of parametric images.

BACKGROUND

Parametric images are commonly used for graphically representing the result of quantitative analyses in diagnostic applications. Particularly, this technique may be used for the assessment of blood perfusion in contrast-enhanced ultrasound imaging. For this purpose, an ultrasound contrast agent (UCA)—for example, consisting of a suspension of phospholipid-stabilized gas-filled microbubbles—is administered to a patient. The contrast agent acts as an efficient ultrasound reflector, and can be easily detected by applying ultrasound waves and measuring the echo signals that are returned in response thereto. Since the contrast agent flows at the same velocity as red-blood cells in the patient, its detection and tracking provides information about blood perfusion in a body-part under analysis. Particularly, the echo signal that is recorded over time for each location of the body-part is associated with a mathematical model function; the model function is used to calculate any desired perfusion parameter (for example, a wash-in rate), which characterizes the location of the body-part. A parametric image is then generated by assigning, to each pixel representing a location of the body-part, the corresponding value of the perfusion parameter (in brief, "perfusion parameter value"). The parametric image shows the spatial distribution of the perfusion parameter values throughout the body-part, so as to facilitate the identification of possible locations thereof that are abnormally perfused (for example, because of a pathological condition).

The parametric images may also be used to perform statistical analysis based on histograms. For example, "Histogram Analysis versus Region of Interest Analysis of Dynamic Susceptibility Contrast Perfusion MR Imaging Data in the Grading of Cerebral Gliomas, M. Law et al., AJNR Am J Neuroradiol 28:761-66, April 2007", which is incorporated by reference, describes the use of this technique in contrast-enhanced Magnetic Resonant (MR) imaging applications. Particularly, a Cerebral Blood Volume (CBV) map is created (being limited between minimum and maximum values required to maintain appropriate color scales). The CBV map is then normalized to a value of unaffected tissue (typically, normal contralateral white matter). A histogram of the values in a Region of Interest (ROI) of the CBV map is now calculated. This histogram is used to assess a grade of a corresponding glioma—for example, based on its standard deviation or on multiple metrics (being identified by means of a binary logistic regression).

Likewise, "Glioma Grading by Using Histogram Analysis of Blood Volume Heterogeneity from MR-derived Cerebral Blood Volume Maps, Kyrre E. Emblem et al., Radiology: Volume 247: Number 3—June 2008, pages 808-817", which is incorporated by reference, describes the calculation of a histogram from a normalized CBV map; a resulting curve is then normalized to the value of one. Glioma malignancy can be assessed by determining a peak height of the histogram distribution (with the result that can be further improved with analysis of the histogram shape).

Moreover, "Histogram Analysis of MR Imaging-Derived Cerebral Blood Volume Maps: Combined Glioma Grading and Identification of Low-Grade Oligodendroglial Subtypes, K. E. Emblem et al., AJNR Am J Neuroradiol 29:1664-70, October 2008", which is incorporated by reference, describes the same technique with the use of a cutoff value for the peak height, in order to identify glioma grades and low-grades oligodendroglial subtypes (even if the authors themselves recognize that the definition of the cutoff value is difficult in practice, so that its transferability is inherently reduced).

As a last example, "Assessing tumour response to treatment: Histogram analysis of parametric maps of tumour vascular function derived from dynamic contrast-enhanced MR images, C. Hayes et al., Proceedings of ISMRM 2000, Denver, Colo., USA, April 2000", which is incorporated by reference, describes the use of statistical analysis of parametric images in contrast-enhanced MR applications (for example, based on permeability) to assess tumor response to treatment. Particularly, this document proposes the use of values of median, range, or skewness (as illustrated qualitatively by the corresponding histograms).

However, when applied to the case of contrast-enhanced ultrasound imaging, the above-described statistical analyses produce results that strongly depend on the equipments that are used to record the echo signals (from which the parametric image is generated); moreover, even when using a given equipment, different results are obtained by varying its settings (for example, gain, log-compression, and so on). Therefore, these results are not suitable for an absolute quantitative evaluation. Moreover, the results cannot be compared among investigators using different equipments or settings.

SUMMARY

In its general terms, an embodiment is based on the idea of applying an auto-scaling procedure.

Particularly, an embodiment proposes a data-processing method for analyzing a body-part (for example, implemented by software). The method includes the step of providing a parametric map (for example, a parametric image of the body-part); the parametric map includes a plurality of parameter values each one characterizing a corresponding location of the body-part (for example, indicative of its wash-in rate). The method continues by determining at least one statistical indicator of at least one distribution of a plurality of analysis parameter values (included in said parameter values) corresponding to selected analysis locations (included in said locations—for example, for a region of interest of the body-part); each statistical indicator is indicative of a condition of an analysis region of the body-part defined by the analysis locations. In an embodiment, the step of determining at least one statistical indicator includes, for each distribution of the analysis parameter values, determining a saturation value. The saturation value partitions an ordered sequence of processing parameter values (included in said parameter values), corresponding to selected processing locations (included in said locations) at least including the analysis locations (for example, consisting of all the locations), into a first subset and a second subset; these subsets consist of a number of the processing parameter values that is determined according to a predefined auto-scaling percentage (for example, in a cumulative histogram of the parametric image). An auto-scaled map (for example, consisting of an auto-scaled image) is then generated. The auto-scaled map includes, for each processing location, an auto-scaled value; the auto-scaled value is equal to the corresponding processing parameter value if included in the second subset, or it is equal to the saturation value if the corresponding processing parameter value is included in the first subset. The at least one statistical indicator is then determined from the auto-scaled values corresponding to the analysis locations (for example, by calculating their histogram, a corresponding probability function, and/or one or more statistical parameters of this probability function).

In an embodiment, each parameter value is indicative of a perfusion of the corresponding location of the body-part that is perfused with a pre-administered contrast agent.

In an embodiment, the processing parameter values of the first subset are higher than (or equal to) the saturation value.

In an embodiment, the step of determining a saturation value includes calculating a cumulative histogram of the processing parameter values, and setting the saturation value to a processing parameter value associated with the auto-scaling percentage in the cumulative histogram.

In an embodiment, the auto-scaling percentage ranges from 80% to 99.99%.

In an embodiment, the step of determining at least one statistical indicator further includes normalizing the auto-scaled values to a predefined normalization range.

In an embodiment, the step of determining at least one statistical indicator includes calculating a histogram of the auto-scaled values corresponding to the analysis locations.

In an embodiment, the step of determining at least one statistical indicator further includes calculating a probability function of the histogram by fitting the histogram with a parametric function (for example, a lognormal function).

In an embodiment, the step of determining at least one statistical indicator includes calculating a value of at least one statistical parameter of the distribution of the analysis parameter values corresponding to the analysis locations.

In an embodiment, the step of calculating a value of at least one statistical parameter includes calculating the value of the at least one statistical parameter from the probability function.

In an embodiment, the processing locations consist of all the locations, and the analysis locations consist of a subset of the locations.

In an embodiment, the at least one statistical parameter is a plurality of statistical parameters (for example, a mode and a standard deviation); in an embodiment, the method further includes the step of displaying an indication of the respective values of the statistical parameters in a graph, which has a visualization dimension for each statistical parameter.

In an embodiment, a knowledge base is provided for storing an indication of at least one set of respective reference ranges for the statistical parameters (for example, by pre-loading it into a mass memory); each set of reference ranges is indicative of a corresponding estimated condition of the body-part. The method further includes the steps of retrieving the at least one set of reference ranges from the knowledge base, and displaying a representation of the at least one set of reference ranges in the graph.

In an embodiment, the at least one distribution of the analysis parameter values corresponding to the analysis locations consists of a plurality of distributions of the analysis parameter values corresponding to the analysis locations, each one for a selected synthesis location (included in said locations); the analysis locations of each synthesis location consist of a subset of the locations including the analysis location. In an embodiment, the method further includes the step of creating a synthesis image; for each synthesis location, the synthesis image includes a synthesis value being based on the corresponding at least one statistical indicator.

In an embodiment, the analysis locations of each synthesis location consist of a pre-defined common number of locations being centered around the synthesis location.

In an embodiment, the at least one statistical indicator of each synthesis location is a respective value of a plurality of statistical parameters of the corresponding distribution of the analysis parameter values (for example, the value of the mode and the value of the standard deviation). A knowledge base is provided for storing an indication of at least one set of respective reference ranges for the statistical parameters; each set of reference ranges is indicative of a corresponding estimated condition of the body-part. The step of creating a synthesis image includes retrieving the at least one set of reference ranges from the knowledge base, and setting the synthesis value of each synthesis location according to a comparison between the values of the statistical parameters of the synthesis location and the at least one set of reference ranges.

In an embodiment, the knowledge base is further adapted to store an indication of a different reference value for each set of reference ranges; the step of creating a synthesis image includes retrieving the at least one reference value from the knowledge base, and setting the synthesis value of each synthesis location to the reference value of the set of reference ranges including the values of the respective statistical parameters of the synthesis location, or to a default value otherwise.

In an embodiment, the synthesis locations consist of all the locations.

A different embodiment proposes a computer program, which includes code means for causing a data-processing system (for example, a computer) to perform the steps of the above-mentioned data-processing method when the computer program is executed on the system.

A further embodiment proposes a corresponding diagnostic system (for example, based on an ultrasound scanner), which includes means specifically configured for performing the steps of the above-mentioned data-processing method.

Another embodiment proposes a configuration method for configuring this diagnostic system. The configuration method starts with the step of providing a plurality of sample parametric maps, which are acquired with different scanners and/or settings thereof; each sample parametric map includes a plurality of sample parameter values, each one characterizing a corresponding sample location of a sample body-part (corresponding to said body-part). The method continues by determining the auto-scaling percentage according to the sample parametric maps.

In an embodiment, the sample parametric maps include a plurality of subsets of the sample parametric maps, each one for a different estimated condition of the sample body-part. The method further includes the steps of determining a sample saturation value for each sample parametric map. The sample saturation value partitions an ordered sequence of the sample parameter values of the sample parametric map into a first sample subset and a second sample subset consisting of a number of sample parameter values that is determined according to the auto-scaling percentage. A plurality of sample auto-scaled maps is then generated each one from a corresponding sample parametric map. The sample auto-scaled map includes, for each sample location of the sample body-part, a sample auto-scaled value; the sample auto-scaled value is equal to the corresponding sample parameter value of the sample parametric map if included in the second sample subset, or it is equal to the sample saturation value if the corresponding sample parameter value of the sample parametric map is included in the first sample subset. The method continues by calculating a plurality of sample statistical parameter values of the distribution of the sample auto-scaled values of each auto-scaled sample map (for example, as above by calculating their histogram and probability function). It is now possible to calculate the set of reference ranges of each estimated condition from the sample statistical parameter values of the corresponding subset of sample parametric maps.

In an embodiment, the method further includes the step of selecting the statistical parameters from the sample statistical parameters or combinations thereof to optimize a differentiation of the estimated conditions.

A different embodiment proposes a computer program, which includes code means for causing a data-processing system (for example, a computer) to perform the steps of the above-mentioned configuration method when the computer program is executed on the system.

A further embodiment proposes a computer program product; the product includes a non-transitory computer readable medium, which embodies a computer program. The computer program includes code means directly loadable into a working memory of a data-processing system, thereby configuring the data-processing system to perform the steps of the above-mentioned data-processing method and/or configuration method.

A different embodiment proposes a diagnostic method for analyzing a body-part of a patient. The diagnostic method includes the step of administering a contrast agent to the patient. An interrogation signal is then applied to the body-part. The method continues by acquiring a sequence of input maps (each one including a plurality of input values, each one indicative of a response to the interrogating signal of a corresponding location of the body-part)—with a parametric function that is then associated with the sequence of input values of each location, a parametric map including a plurality of parameter values each one characterizing a corresponding location of the body-part that is calculated by setting each parameter value according to the corresponding parametric function, and the parametric map that is processed according to the above-mentioned data-processing method to obtain the at least one statistical indicator of the at least one analysis region. At this point, a condition of the body-part is evaluated according to the at least one statistical indicator of the at least one analysis region.

BRIEF DESCRIPTION OF THE DRAWINGS

One or more embodiments, as well as features and the advantages thereof, will be best understood with reference to the following detailed description, given purely by way of a non-restrictive indication, to be read in conjunction with the accompanying drawings (wherein corresponding elements are denoted with equal to similar references, and their explanation is not repeated for the sake of exposition brevity). Particularly.

DETAILED DESCRIPTION

Figure 1:
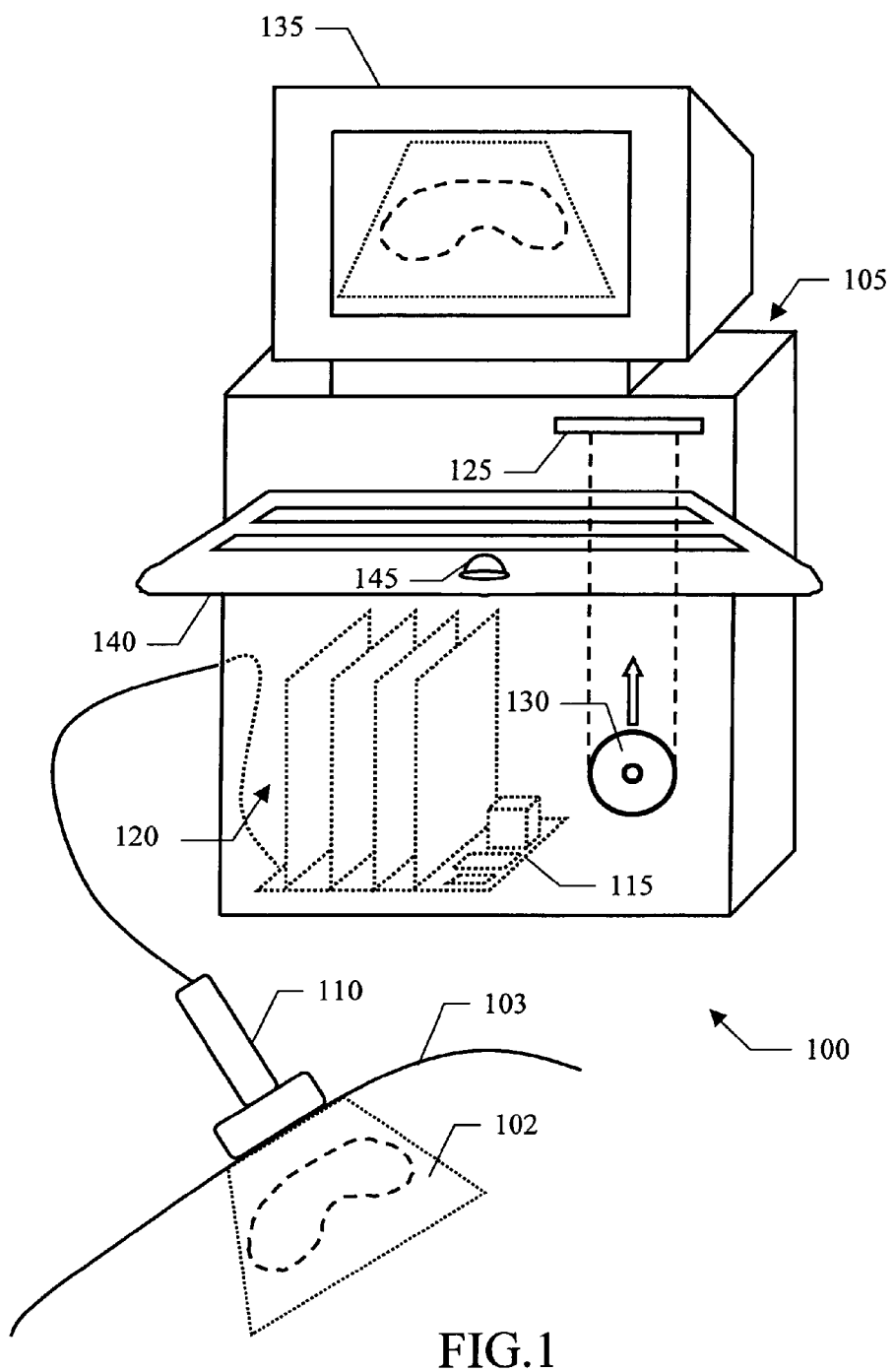
FIG. 1 is a pictorial representation of a diagnostic system in which an embodiment is applicable.

With reference in particular to FIG. 1, a diagnostic system (i.e., a medical imaging system) consisting of an ultrasound scanner 100 is illustrated; the scanner 100 may be used to analyze a body-part 102 of a patient 103 in an embodiment. The ultrasound scanner 100 includes a central unit 105 and a hand-held transmit-receive imaging probe 110 (for example, of the array type). The imaging probe 110 transmits ultrasound waves consisting of a sequence of pulses (for example, having a center frequency between 1 and 50 MHz), and receives radio-frequency (RF) echo signals resulting from the reflection of the ultrasound pulses by the body-part 102; for this purpose, the imaging probe 110 is provided with a transmit/receive multiplexer, which allows using the imaging probe 110 in the above-described pulse-echo mode.

The central unit 105 houses a motherboard 115, on which the electronic circuits controlling operation of the ultrasound scanner 100 (for example, a microprocessor, a working memory and a hard-disk drive) are mounted. Moreover, one or more daughter boards (denoted as a whole with 120) are plugged into the motherboard 115; the daughter boards 120 provide the electronic circuits for driving the imaging probe 110 and for processing the received echo signals. The ultrasound scanner 100 can also be equipped with a drive 125 for accessing removable disks 130 (such as CDs or DVDs). A monitor 135 displays images relating to an analysis process that is in progress. Operation of the ultrasound scanner 100 is controlled by means of a keyboard 140, which is connected to the central unit 105 in a conventional manner; preferably, the keyboard 140 is provided with a trackball 145 that is used to manipulate the position of a pointer (not shown in the figure) on a screen of the monitor 135.

During the analysis of the body-part 102, a contrast agent (acting as an efficient ultrasound reflector) is administered to the patient 103. For example, the contrast agent consists of a suspension of gas bubbles in a liquid carrier; typically, the gas bubbles have diameters on the order of 0.1-5 µm, so as to allow them to pass through the capillaries of the patient. The gas bubbles are generally stabilized by entraining or encapsulating the gas or a precursor thereof into a variety of systems, including emulsifiers, oils, thickeners, sugars, proteins or polymers; stabilized gas bubbles are generally referred to as gas-filled microvesicles. The microvesicles include gas bubbles dispersed in an aqueous medium and bound at the gas/liquid interface by a very thin envelope involving a surfactant—i.e., an amphiphilic material (also known as microbubbles). Alternatively, the microvesicles include gas bubbles that are surrounded by a solid material envelope formed of lipids or of natural or synthetic polymers (also known as microballoons or microcapsules). Another kind of contrast agent includes a suspension of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising gas-filled microvesicles is SonoVue® by Bracco International BV.

The contrast agent may be administered to the patient 103 intravenously as a bolus—i.e., a single dose provided by hand with a syringe over a short period of time (of the order of 2-20 seconds). The contrast agent circulates within a vascular system of the patient 103, so as to perfuse the body-part 102. At the same time, the imaging probe 110 is placed in contact with the skin of the patient 103 in the area of the body-part 102. A series of ultrasound pulses with low acoustic energy (such as with a mechanical index MI=0.01-0.1) is applied to the body-part 102, so as to involve a negligible destruction of the contrast agent (such as less than 5%, and preferably less than 1% of its local concentration between successive ultrasound pulses). A sequence of echo signals that is recorded for each location of the body-part 102 in a selected scanning plane, in response to the ultrasound pulses at corresponding acquisition instants over time (for example, with a rate of 10-30 acquisitions per second), provides a representation of the location of the body-part in a slice thereof during the analysis process. The echo signals result from the superimposition of different contributions generated by the contrast agent (if present) and the surrounding tissue. The ultrasound scanner 100 may operate in a contrast-specific imaging mode so as to substantially remove, or at least reduce, the dominant (linear) contribution of tissue in the echo signals, with respect to the (non-linear) contribution of the contrast agent; examples of contrast-specific imaging modes include harmonic imaging (HI), pulse inversion (PI), power modulation (PM) and contrast pulse sequencing (CPS) techniques, as described, for example, in "Rafter et al., Imaging technologies and techniques, Cardiology Clinics 22 (2004), pp. 181-197" (the entire disclosure of which is herewith incorporated by reference).

One or more parametric images are then generated from the recorded echo signals. Each parametric image is defined by a matrix (for example, with M=512 rows and N=512 columns) of values for respective visualizing elements—i.e., basic picture elements (pixels), each one corresponding to a location of the body-part 102 (in brief, "pixel value"). Each pixel represents the value of a perfusion parameter (in brief, "perfusion parameter value"), which is calculated for the location of the body-part from the corresponding sequence of echo signals—for example, the value of its wash-in rate (in brief, "wash-in rate value").

For example, a sequence of parametric images may be generated in real-time as described in EP08169794.8 (the entire disclosures of which is herein incorporated by reference). Briefly, each sequence of echo signals is filtered by applying a Maximum Intensity Projection (MIP) algorithm, wherein the echo signals are held at their maximum value over time. The sequence of filtered echo signals is then monitored in order to detect its peak (as soon as the filtered echo signals remain constant for a predefined stability time-window). The wash-in rate value of the corresponding location of the body-part can now be calculated as the ratio between the value of the filtered echo signal at its peak and a wash-in duration (determined as the difference between an instant of the peak and an instant of contrast-agent arrival). The parametric image is then generated by assigning, to each pixel, the wash-in rate value of its location of the body part.

Figure 2B:
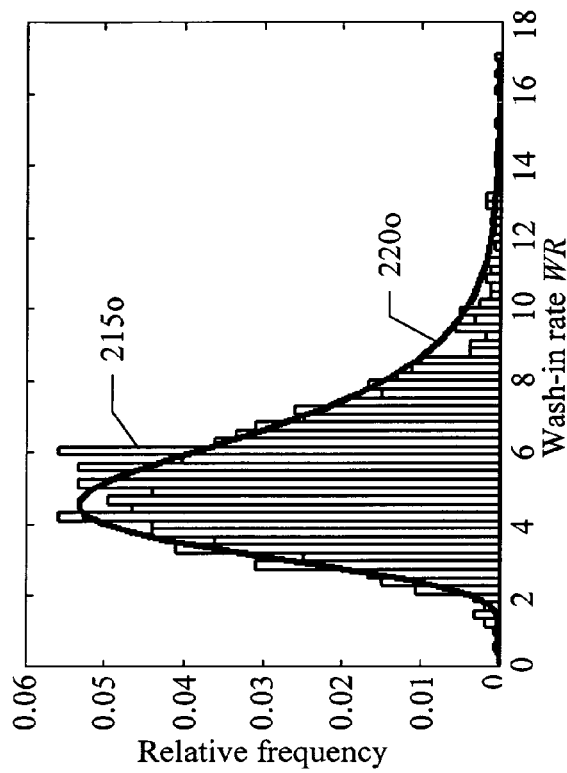
FIG. 2A-2E show an example of auto-scaling according to an embodiment.
Figure 2A:
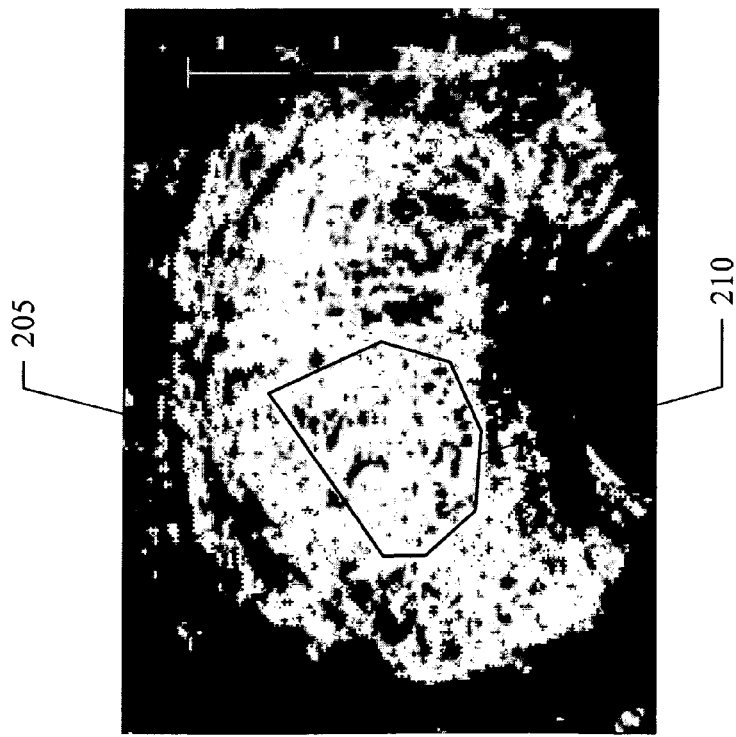

Moving to FIG. 2A, a generic parametric image (denoted with 205) is shown for wash-in rate values WR(x,y)—in brief, "WR"—of the pixels identified by the spatial coordinates x,y in the parametric image 205 (row number and column number, respectively). Such a parametric image may be used to perform a statistical analysis of a selected region of interest 210 of the body-part.

For this purpose, as shown in FIG. 2B, a histogram is calculated for the wash-in rate values WR of the pixels inside the region of interest. In detail, an ordered sequence of the wash-in rate values WR (ranging from a minimum value WRmin=0 to a maximum value WRmax=17) is split into a predefined number of adjacent, non-overlapping bins (for example, each one with a width between 1 and 5). Each pixel in the region of interest is assigned to the bin including its wash-in rate value WR; each bin is then associated with a relative frequency of the wash-in rate values WR, as defined by dividing a count of the bin by a total count in the whole region of interest 210—so as to make it independent of the size of the region of interest 210. The histogram is generally represented with a graph 215o, which plots the bins on the abscissa-axis and the relative frequency on the ordinate-axis. Each bin is represented with a bar, which has a height proportional to its relative frequency—with a total relative frequency of all the bars that is always equal to 1. The histogram (denoted with the same reference 215o) then represents a distribution of the wash-in rate values WR in the region of interest.

A probability function F(WR) of the wash-in rate values WR may then be associated with the histogram 215o. For example, this is achieved by fitting the histogram 215o with a log normal function log n(WR) (i.e., a normal probability function of the natural logarithm of the independent variable WR), i.e.:

$$\log n(WR) = \frac{e^{-\frac{[ln(WR)-m]^2}{2s^2}} WR_{width}}{WR \cdot s\sqrt{2\pi}},$$

where the (fitting) parameters m and s are the mean and standard deviation of the distribution of the variable ln(WR), respectively, and $WR_{width}$ is the bin width. More in detail, the probability function F(WR) consists of an actual instance of the log normal function log n(WR)—defined by corresponding values of its fitting parameters m and s (in brief, "fitting parameters values" m and s)—which is determined by an optimization process selecting the parameters values m and s that provide the best fitting of the histogram 215o. The probability function F(WR) is represented with a curve 220o that approximates the histogram 215o. The probability function F(WR) (denoted with the same reference 220O) then smoothes the distribution of the wash-in rate values WR in the region of interest, so as to facilitate its analysis. Moreover, it is now possible to maintain an arbitrarily high number of bins of the histogram 215o, so as to increase the accuracy of the analysis (with the corresponding greater noise that is filtered out by the above-mentioned smoothing).

Figure 2D:
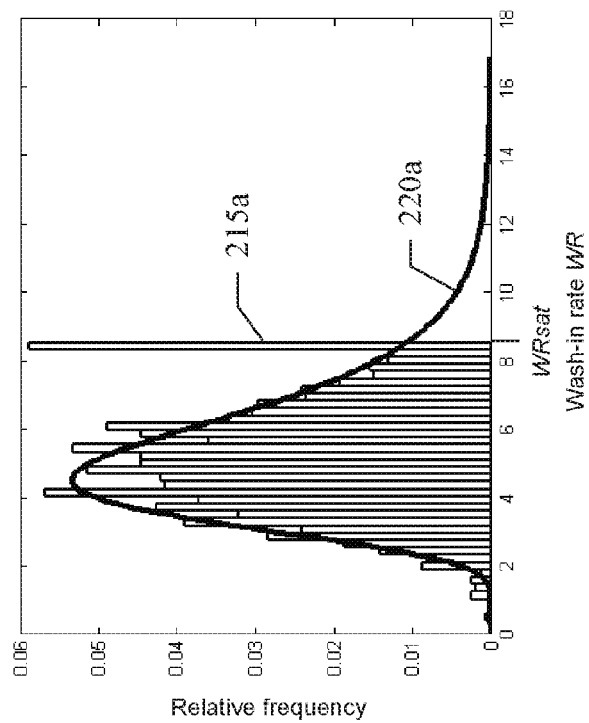
Figure 2C:
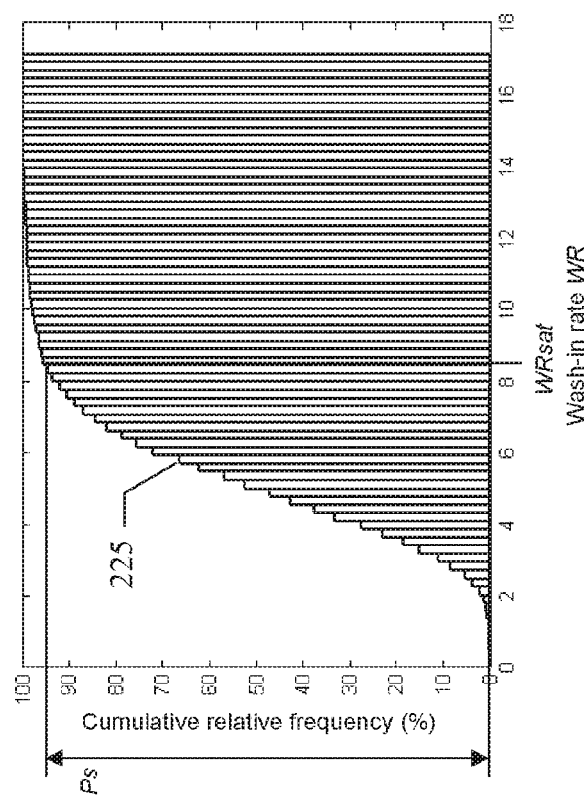

With reference now to FIG. 2C, in an embodiment, the parametric image is auto-scaled before calculating the histogram. For this purpose, a cumulative histogram is calculated for the wash-in rate values WR of all the pixels in the parametric image; in this case, each bin is associated with a cumulative relative frequency of the wash-in rate values WR in all the bins up to it. The cumulative histogram is likewise represented with a graph 225, which plots the bins on the abscissa-axis and the cumulative relative frequencies (expressed in percentage) on the ordinate-axis (with a height of each bar that is now proportional to its cumulative relative frequency up to a last bar having a cumulative relative frequency equal to 100%). The cumulative histogram (denoted with the same reference 225) is used to determine a saturation value WRsat for the wash-in rate values WR; the saturation value WRsat is equal to the wash-in rate value WR associated with a predefined auto-scaling percentage Ps of the cumulative relative frequency in the cumulative histogram 225. The auto-scaling percentage Ps may be set to a value between 80% and 99.99%, for example, to a value approximately between 90% and 99.9% (such as approximately equal to 95%). For example, in the figure the saturation value is WRsat=8.5 (as determined by a central wash-in rate value WR of the last bin having a cumulative relative frequency at least equal to the auto-scaling percentage Ps—i.e., intercepted by a horizontal line at its value).

The parametric image is then auto-scaled by setting all the wash-in rate values WR higher than the saturation value WRsat equal to it. Therefore, as shown in FIG. 2D, a histogram 215a of the same region of interest for the (auto-scaled) parametric image is clipped to the saturation value WRsat—introducing a peak of the relative frequency (corresponding to the auto-scaling percentage Ps) at the saturation value WRsat. As above, a probability function 220a is then associated with the histogram 215a.

Figure 2E:
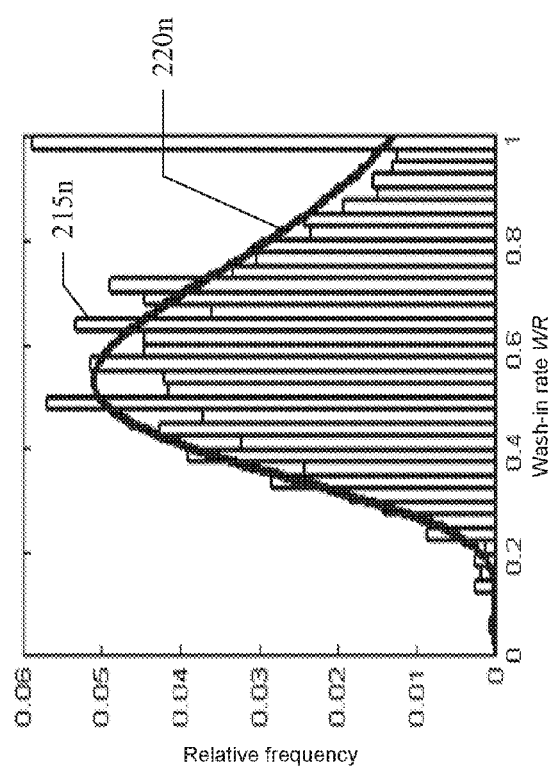

Moving to FIG. 2E, the wash-in rate values WR are normalized (if it is necessary) to a common normalization range. Particularly, each (original) wash-in rate value WR—ranging from the (original) minimum value WRmin to the saturation value WRsat—is replaced with a normalized value—ranging from a normalized minimum value WRmin(n) to a normalized maximum value WRmax(n) (for example, from 0 to 1)—given by:

$$\frac{WR - WRmin}{WRsat - WRmin} \times (WRmax(n) - WRmin(n)) + WRmin(n),$$

and then (when WRmin=WRmin(n)=0):

$$\frac{WR}{WRsat} \times WRmax(n).$$

In this way, there is obtained a histogram 215n (for the same region of interest of the auto-scaled and normalized parametric image), which is associated with a probability function 220n.

The auto-scaling (and the optional normalization) of the parametric image effectively results in an equalization of the histogram that is obtained from any region of interest thereof, and therefore of the corresponding probability function. It has been surprisingly reckoned that this equalization strongly reduces a dependency on the ultrasound scanner (and on its settings, such as the gain) used to generate the parametric image. Therefore, the probability function can now be used to perform statistical analyses that are substantially independent of the ultrasound scanners and their settings (so as to provide absolute quantitative assessments). In this way, the obtained results can be compared among investigators using different ultrasound scanners or settings.

It is emphasized that this result is achieved in a completely dynamic way. Indeed, the saturation value WRsat is not fixed a priori, but it is recalculated for each parametric image according to the auto-scaling percentage Ps (so as to depend on its actual wash-in rate values WR).

Figure 3B:
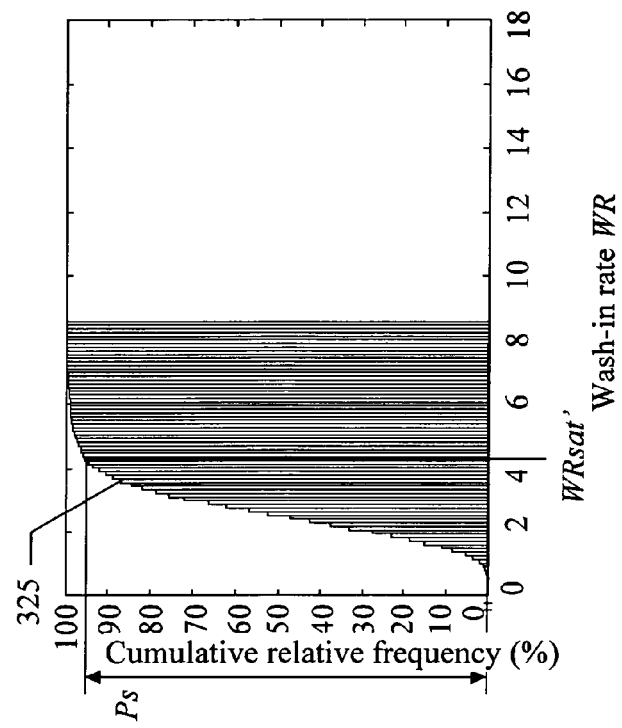
FIG. 3A-3C show an example of auto-scaling according to another embodiment.
Figure 3A:
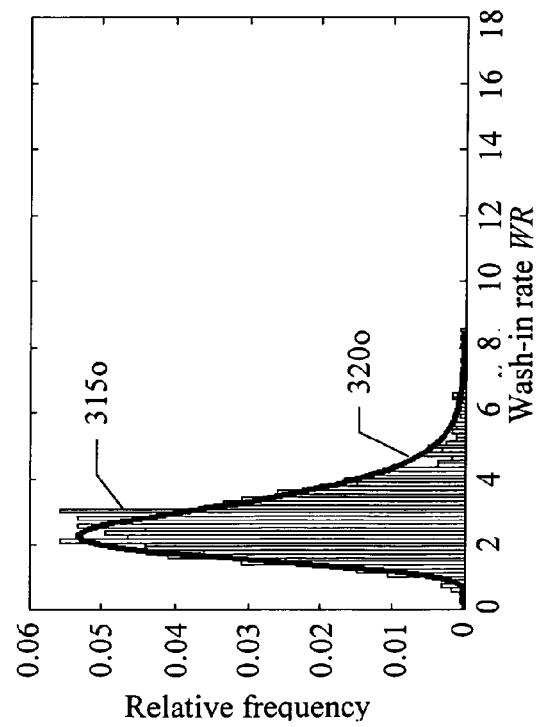

For example, FIG. 3A shows a histogram 315o and a corresponding probability function 320o that are obtained for the same region of interest as above from another parametric image (not shown in the figure). In this case, the parametric image is generated with an ultrasound scanner having a lower sensitivity, or with the same ultrasound scanner being set to a lower gain. Therefore, the wash-in rate values WR are lower, so that the histogram 315o and the probability function 320o are quite different from the previous ones (see FIG. 2B); particularly, they have a position of their peak that is shifted to the left (i.e., towards lower wash-in rate values WR) and they are narrower (i.e., with a lower variation of the wash-in rate values WR)—ranging from a minimum value WRmin'=0, as above, to a maximum value WRmax'=9, far lower than the maximum value WRmax=17 above).

Therefore, as shown in FIG. 3B, a saturation value WRsat' that is determined from a corresponding cumulative histogram 325 for the same auto-scaling percentage Ps=95% is now lower than before (i.e., WRsat'=4.3 instead of WRsat=8.5).

Figure 3C:
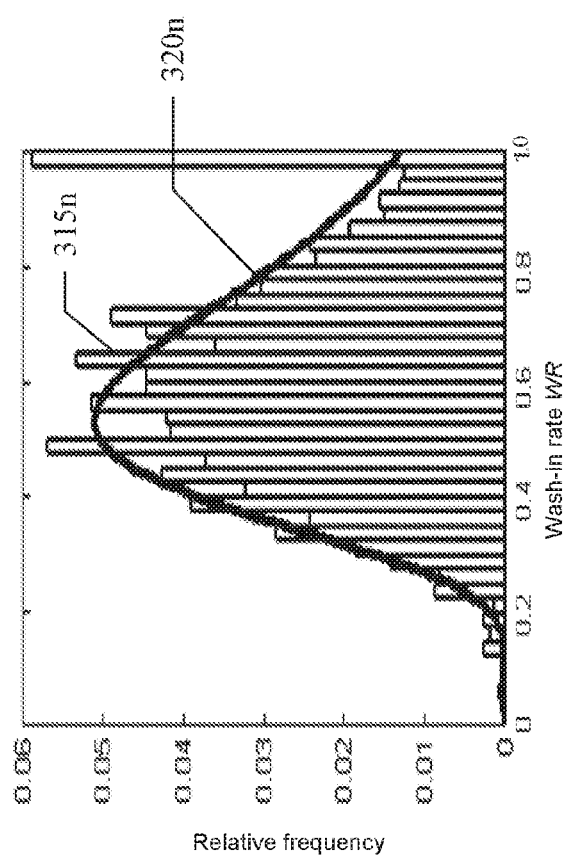

With reference now to FIG. 3C, a histogram 315n and a corresponding probability function 320n that are then obtained from the parametric image after its auto-scaling (according to this saturation value WRsat') and normalization (from the same normalized minimum value WRmin(n) to the same normalized maximum value WRmax(n)) have their peak that is shifted to the right (i.e., towards higher wash-in rate values WR) and they are wider (i.e., with a larger variation of their wash-in rate values WR); as a result, the histogram 315n and the probability function 320n become substantially the same as the previous ones (see FIG. 2E).

Different examples of in-vivo applications of the above-described technique are illustrated in FIG. 4A-4H. Considering in particular FIG. 4A, a parametric image 405 of a healthy prostate (with normal tissue) is shown. Four regions of interest are selected in the parametric image 405; particularly, a region of interest 410pl and a region of interest 410pr are selected for a left and a right Peripheral Zone (PZ) of the prostate, respectively, and a region of interest 410tl and a region of interest 410tr are selected for a left and a right Transitional Zone (TZ) of the prostate, respectively. The parametric image 405 is auto-scaled and normalized, and four histograms (not shown in the figure) are calculated for the regions of interest 410pl, 410pr, 410tl and 410tr.

Figures 4A, 4B:
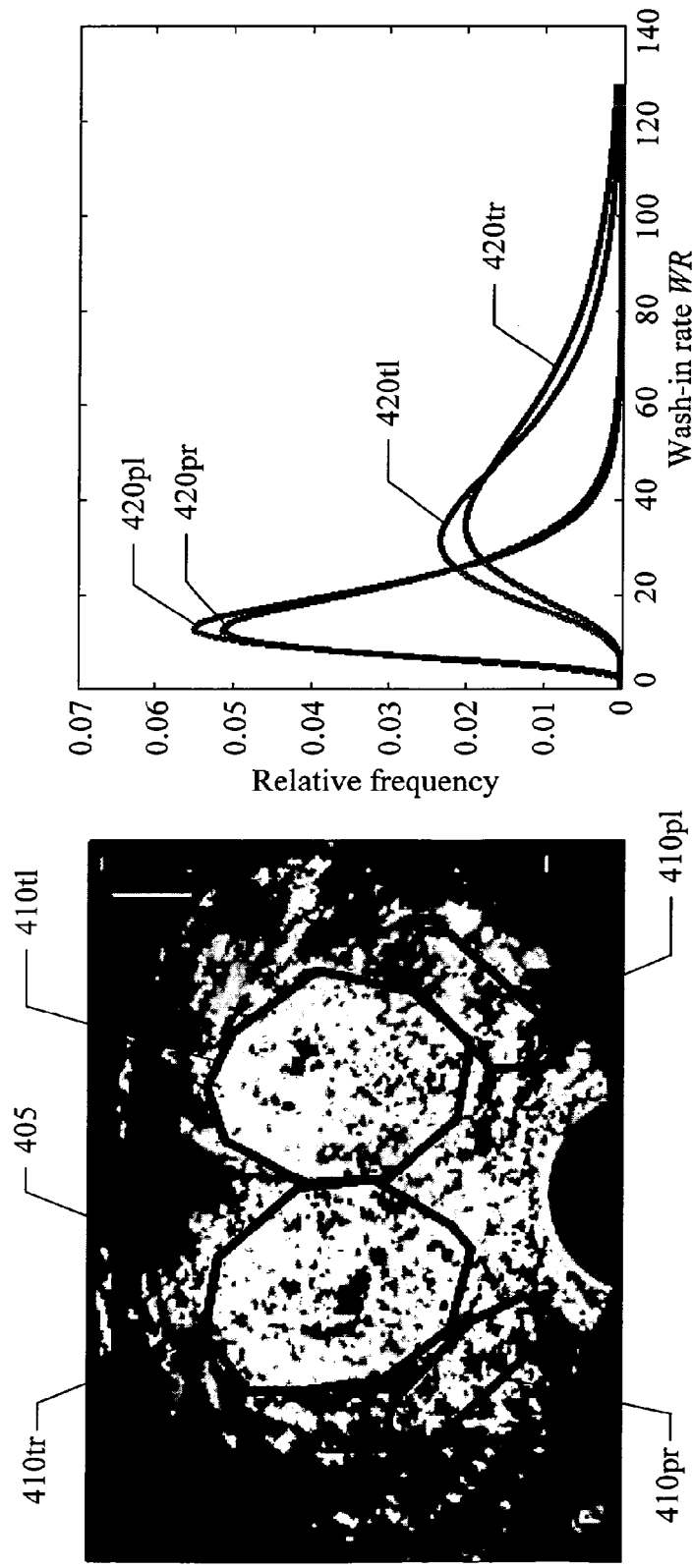
FIG. 4A-4H are illustrative examples of in-vivo applications of an embodiment.

Moving to FIG. 4B, four probability functions are then determined by curve fitting from these histograms, so as to obtain a probability function 420pl for the left PZ, a probability function 420pr for the right PZ, a probability function 420tl for the left TZ, and a probability function 420tr for the right TZ. As can be seen, the two probability functions 420pl and 420pr for the PZ on either side of the prostate are very similar and almost overlap; also, the two probability functions 420tl, 420tr for the TZ on either side of the prostate are very similar and almost overlap. Conversely, the probability functions 420pl, 420pr and 420tl, 420tr (for the PZ and the TZ, respectively) are significantly different.

Figure 4C:
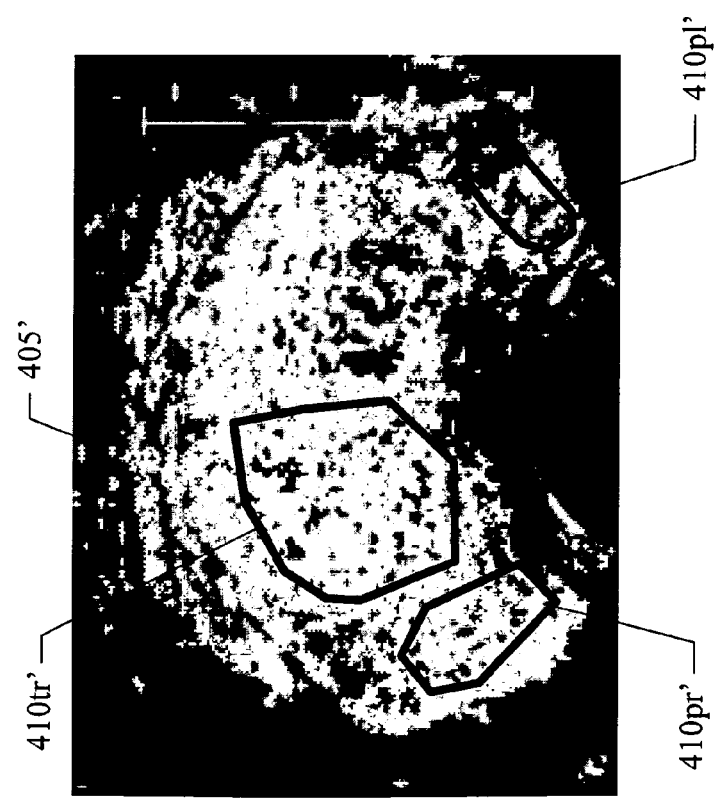

With reference now to FIG. 4C, a parametric image 405' of a prostate in a pathological condition is shown. Three regions of interest are selected in the parametric image 405'. Particularly, a region of interest 410pr' is selected in the right PZ with a malignant lesion consisting of Prostate Cancer (PCa); a region of interest 410pl' and a region of interest 410tr' are selected in the left PZ and the right TZ, respectively, with normal tissue. The parametric image 405' is auto-scaled and normalized, and three histograms (not shown in the figure) are calculated for the regions of interest 410pr', 410pl' and 410tr'.

Figure 4D:
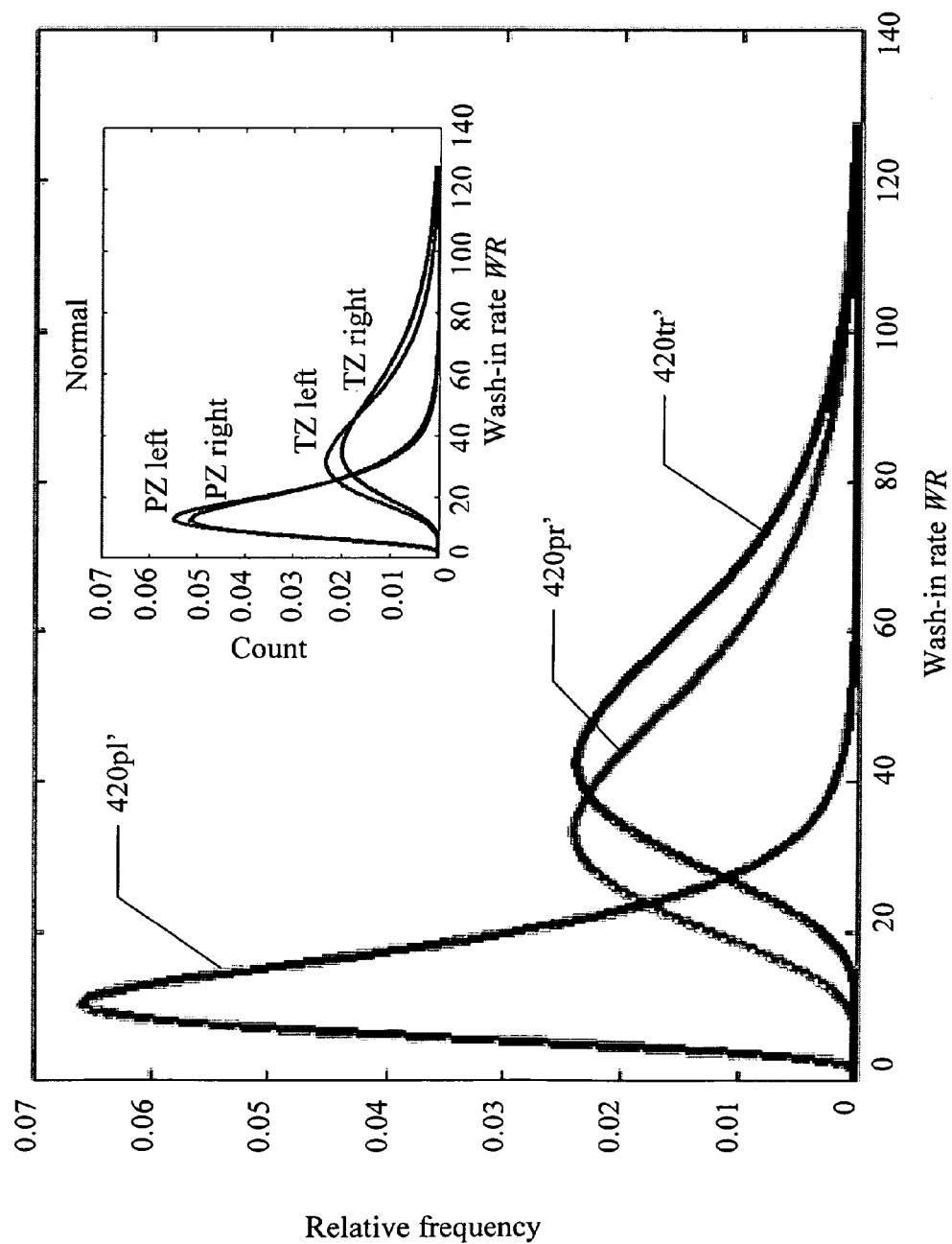

Moving to FIG. 4D, three probability functions are then determined by curve fitting from these histograms, so as to obtain a probability function 420pr' for the right PZ, a probability function 420pl' for the left PZ, and a probability function 420tr' for the right TZ. As can be seen, the probability functions 420pl' and 420tr' (for normal tissue in the PZ and the TZ, respectively) are very similar to the corresponding ones obtained from the same zones in the healthy prostate (as shown in FIG. 4B and being repeated in the insert at the top-right corner). Conversely, the probability function 420pr' for PCa is very different in shape compared to the one obtained in FIG. 4B from the same zone in the healthy prostate (representing normal tissue); particularly, the probability function 420pr' has a lower value of its peak, has a position of the peak that is shifted to the right, and it is wider. Therefore, based on the analysis of the probability function 420pr', the corresponding malignant lesion in the PZ can be easily differentiated from normal tissue in the PZ.

Figure 4E:
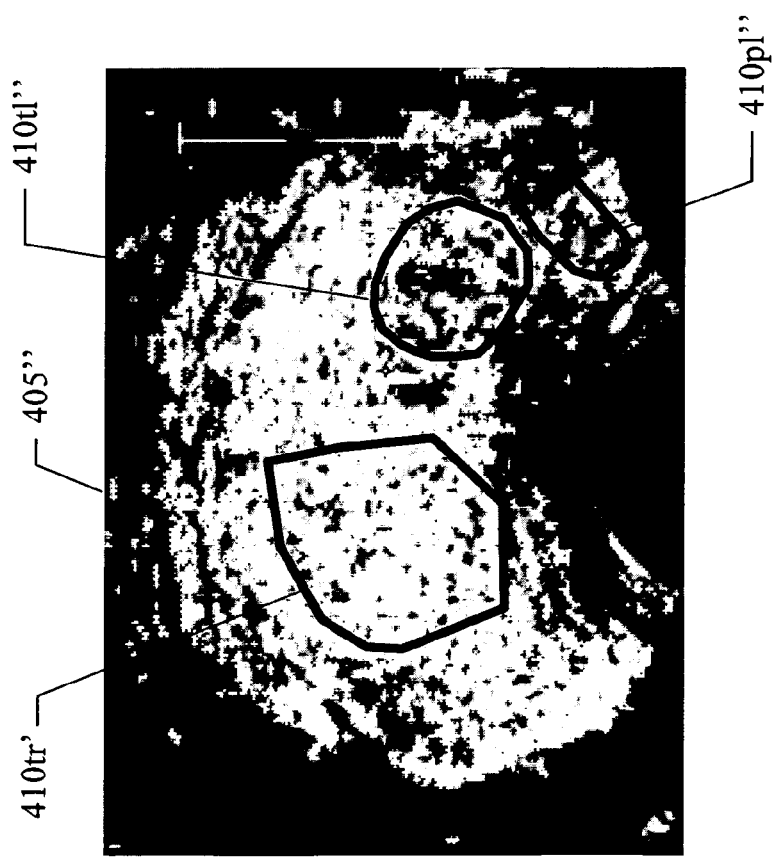

Considering FIG. 4E, a parametric image 405" of a prostate in another pathological condition is shown. Three regions of interest are selected in the parametric image 405". Particularly, a region of interest 410tl" is selected in the left TZ with a benign lesion consisting of an adenoma (Benign Prostate Hyperplasia, or BPH); a region of interest 410pl" and a region of interest 410tr" are selected in the left PZ and the right TZ, respectively, with normal tissue. The parametric image 405" is auto-scaled and normalized, and three histograms (not shown in the figure) are calculated for the regions of interest 410tl", 410pl" and 410tr".

Figure 4F:
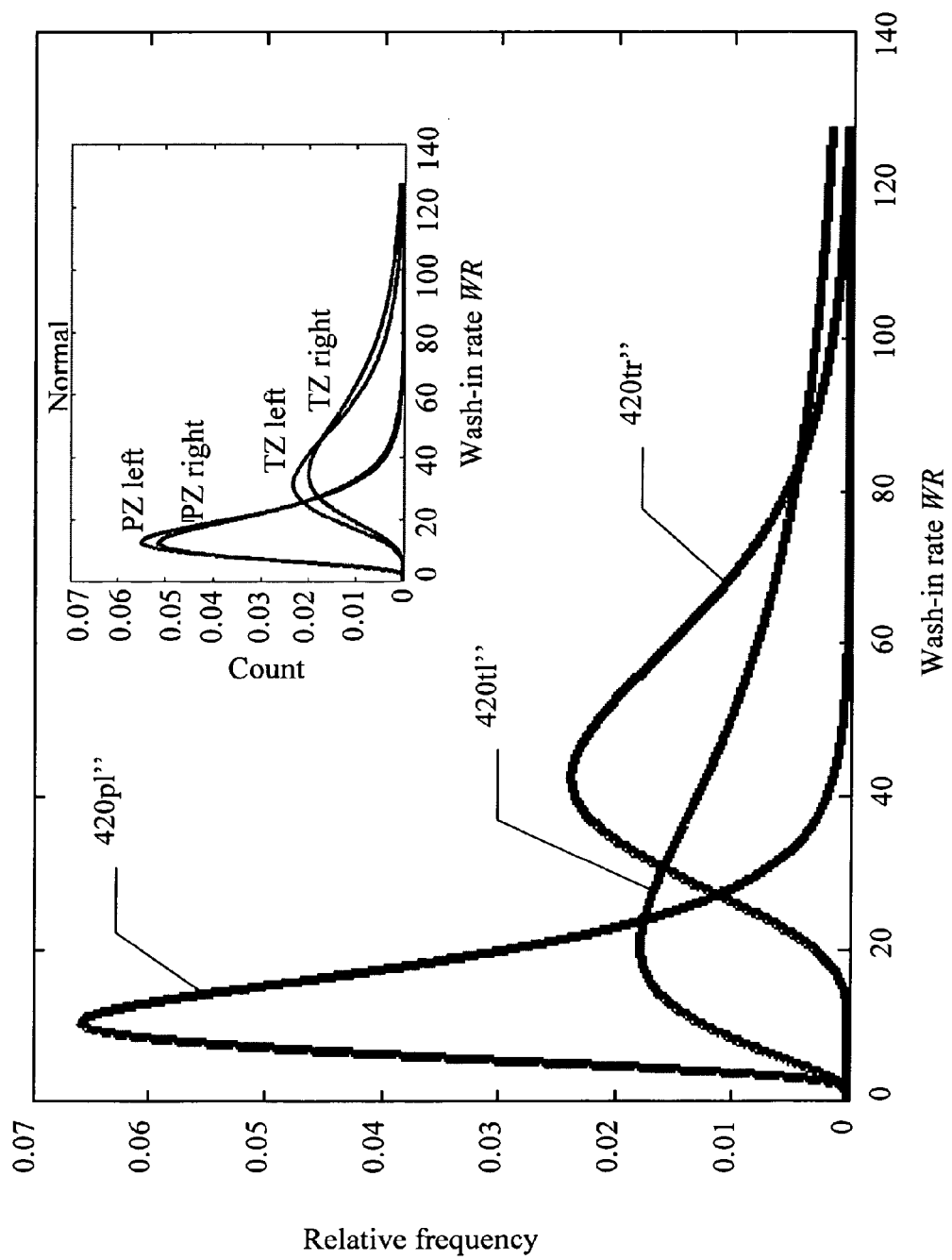

Moving to FIG. 4F, three probability functions are then determined by curve fitting from these histograms, so as to obtain a probability function 420tl" for the left TZ, a probability function 420pl" for the left PZ, and a probability function 420tr" for the right TZ. As can be seen, the probability functions 420pl" and 420tr" (for normal tissue) are again very similar to the corresponding ones obtained from the same zones in the healthy prostate (as shown in FIG. 4B and being repeated in the insert at the top-right corner). Conversely, the probability function 420tl" for BPH is very different in shape compared to the one obtained in FIG. 4B from the same zone in the healthy prostate (representing normal tissue); particularly, the probability function 420tl" has a position of its peak that is shifted to the left and it is wider. Therefore, based on the analysis of the probability function 420tl", the corresponding benign lesion in the TZ can be easily differentiated from normal tissue in the TZ; at the same time, the probability function 420tl" for BPH also differs from the one for PCa of FIG. 4D (since it is more skewed to the right); such a difference can be used for lesion characterization in the TZ—i.e. differentiating benign lesions from malignant lesions.

Figure 4G:
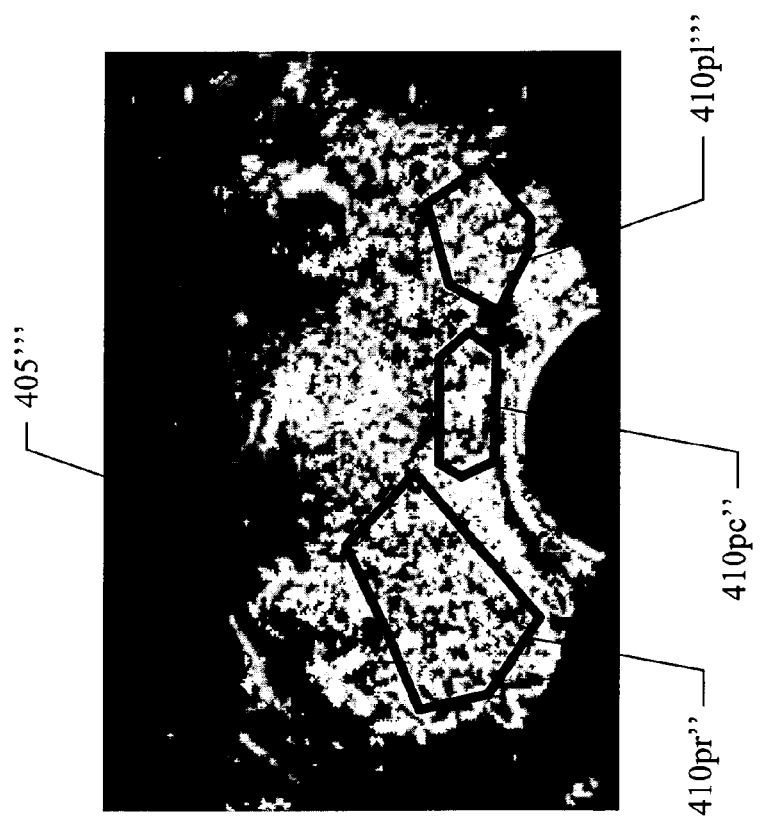

Finally, considering FIG. 4G, a parametric image 405''' of a prostate in a different pathological condition is shown. Three regions of interest are selected in the parametric image 405'''. Particularly, a region of interest 410pl''' and a region of interest 410pr''' are selected in the left and the right PZ, respectively, with a benign lesion consisting of Prostatitis; a region of interest 410pc''' is instead selected in a central PZ with normal tissue. The parametric image 405''' is auto-scaled and normalized, and three histograms (not shown in the figure) are calculated for the regions of interest 410pl''', 410pr''' and 410pc'''.

Figure 4H:
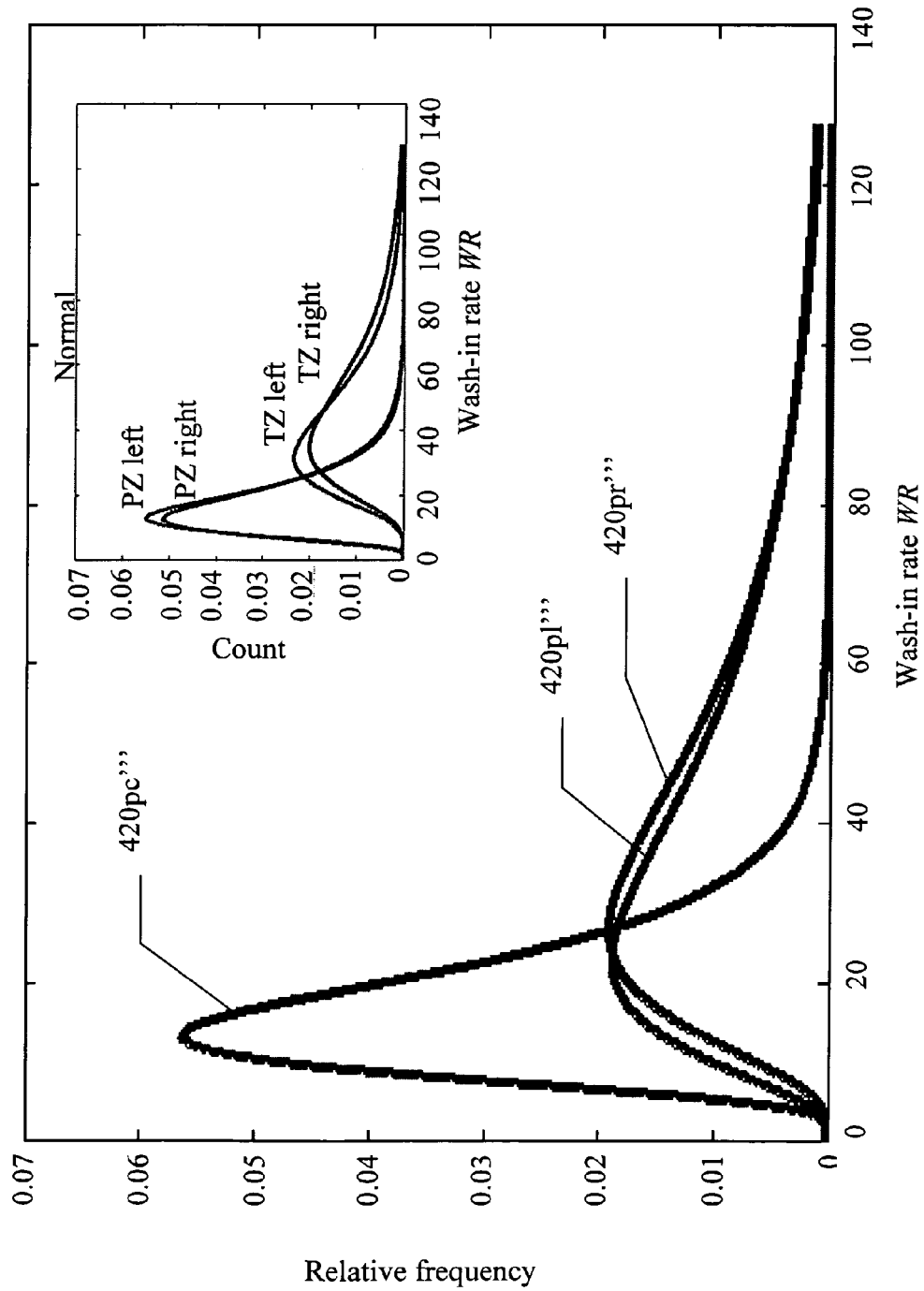

Moving to FIG. 4H, three probability functions are then determined by curve fitting from these histograms, so as to obtain a probability function 420pl''' for the left PZ, a probability function 420pr''' for the right PZ, and a probability function 420pc''' for the central PZ. As can be seen, the probability function 420pc''' (for normal tissue) is again very similar to the corresponding one obtained from the healthy prostate (as shown in FIG. 4B and being repeated in the insert at the top-right corner). Conversely, the probability functions 420pl''' and 420pr''' for Prostatitis are very different in shape compared to the probability function 420pc'''. Therefore, based on the analysis of the probability functions 420pl''' and 420pr''', the corresponding benign lesion in the PZ can be easily differentiated from normal tissue in the PZ; at the same time, the probability functions 420pl''' and 420pr''' for Prostatitis also differ from the one for PCa of FIG. 4D; in this case as well, such difference can be used for lesion characterization in the PZ (to differentiate benign lesions from malignant lesions).

An embodiment of the above-described procedure (making possible to perform the above-described qualitative comparison of the probability functions, irrespectively of the ultrasound scanner, or its settings, that is used to generate the parametric images) strongly facilitates the task of a physician.

Each probability function can also be used to perform a (quantitative) statistical analysis of the distribution of the wash-in rate values WR in the corresponding region of interest. For this purpose, it is possible to calculate the respective value of different statistical parameters of the probability function F(WR) (in brief, "statistical parameters values"). Examples of such statistical parameters are a mean mean (WR) (representing a center of gravity of the distribution of the wash-in rate values WR), a mode mod(WR) (representing the wash-in rate value WR at a peak of the probability function F(WR)—i.e., the most frequently occurring wash-in rate value WR), a median med(WR) (representing a middle value of the wash-in rates WR—i.e., the wash-in rate value WR such that an equal number of wash-in rate values WR are less than and greater than it), a standard deviation σ(WR) (representing a variability or dispersion of the wash-in rate values WR around their mean), and a skewness γ(WR) (representing an asymmetry of the distribution of the wash-in rate values WR). These statistical parameters values can be calculated from the fitting parameters values m and s of the probability function F(WR) by:

$$\text{mean}(WR) = e^{m+\frac{s^2}{2}},$$

$$\text{mod}(WR) = e^{m-s^2},$$

$$\text{med}(WR) = e^m,$$

$$\sigma(WR) = \sqrt{e^{s^2+2m}(e^{s^2}-1)},$$

and $$\gamma(WR) = \sqrt{e^{s^2}-1}(2+e^{s^2}).$$

The statistical parameters values are useful to identify pathological conditions in the region of interest of the body-part under analysis; particularly, they allow differentiating normal tissue from lesions, and malignant lesions from benign lesions. Moreover, it is also possible to monitor the evolution of a pathological condition or the response to a treatment by successive measurements of the same statistical parameters in the same region of interest of the body-part over time. This further facilitates the task of the physician.

In an embodiment, a combination of two or more statistical parameters (such as the mode mod(WR) and the standard deviation σ(WR)) is exploited. For example, 23 patients were analyzed with different ultrasound scanners; more specifically, 18 patients were analyzed with a Philips iU22, 4 patients were analyzed with a Siemens Sequoia and 1 patient was analyzed with a Toshiba Aplio. For each patient, a parametric image of his prostate was generated (and then auto-scaled and normalized). Corresponding histograms and probability functions F(WR) were determined for 83 regions of interest in these parametric images. These regions of interest belong to different categories of the body-part, or zones thereof (as defined by their position and/or condition); particularly, the probability functions were determined in the PZ for 26 regions of interest with normal tissue, 2 regions of interest with Prostatitis, and 31 regions of interest with PCa, and they were determined in the TZ for 21 regions of interest with normal tissue, and 2 regions of interest with BPH. For each probability function F(WR), the corresponding value of the mode mod(WR) and of the standard deviation σ(WR)—in brief, "mode value" mod(WR) and "standard deviation value" σ(WR)—were calculated.

Figure 5A:
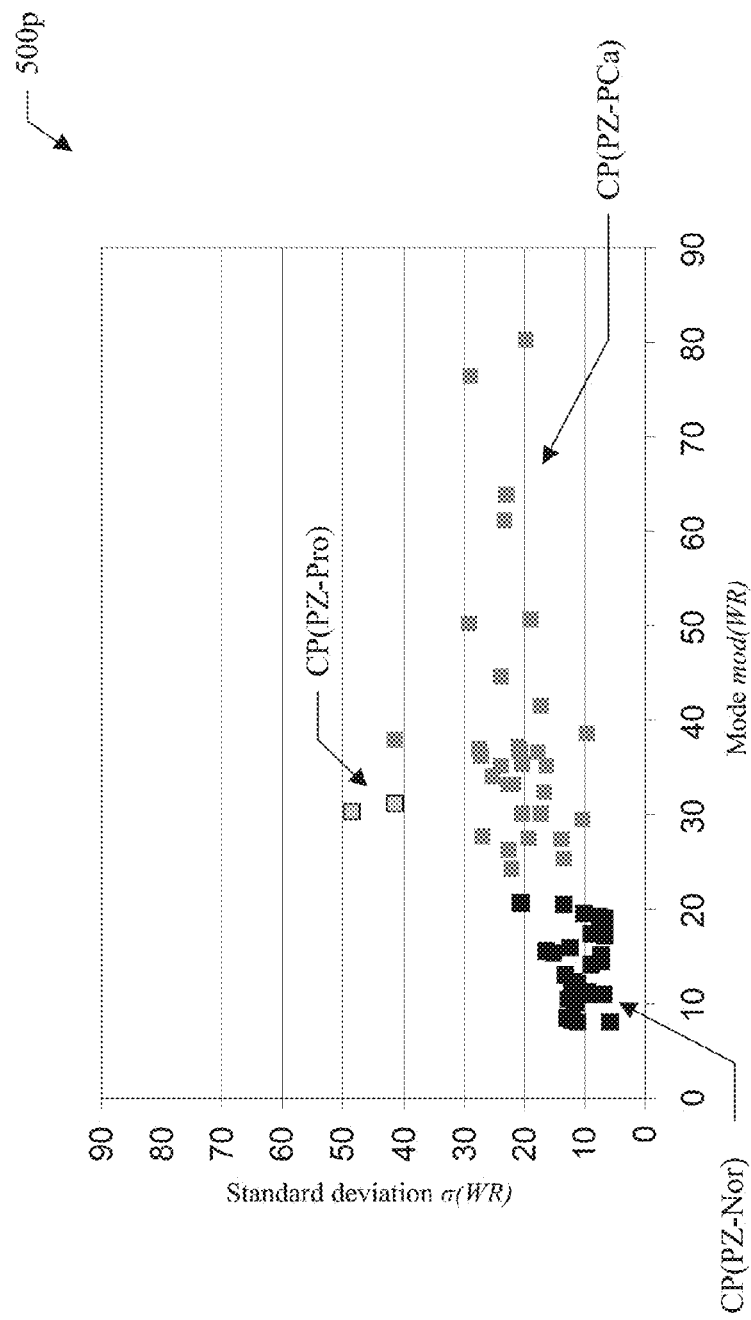
FIG. 5A-5E show examples of statistical analyses according to an embodiment.
Figure 5B:
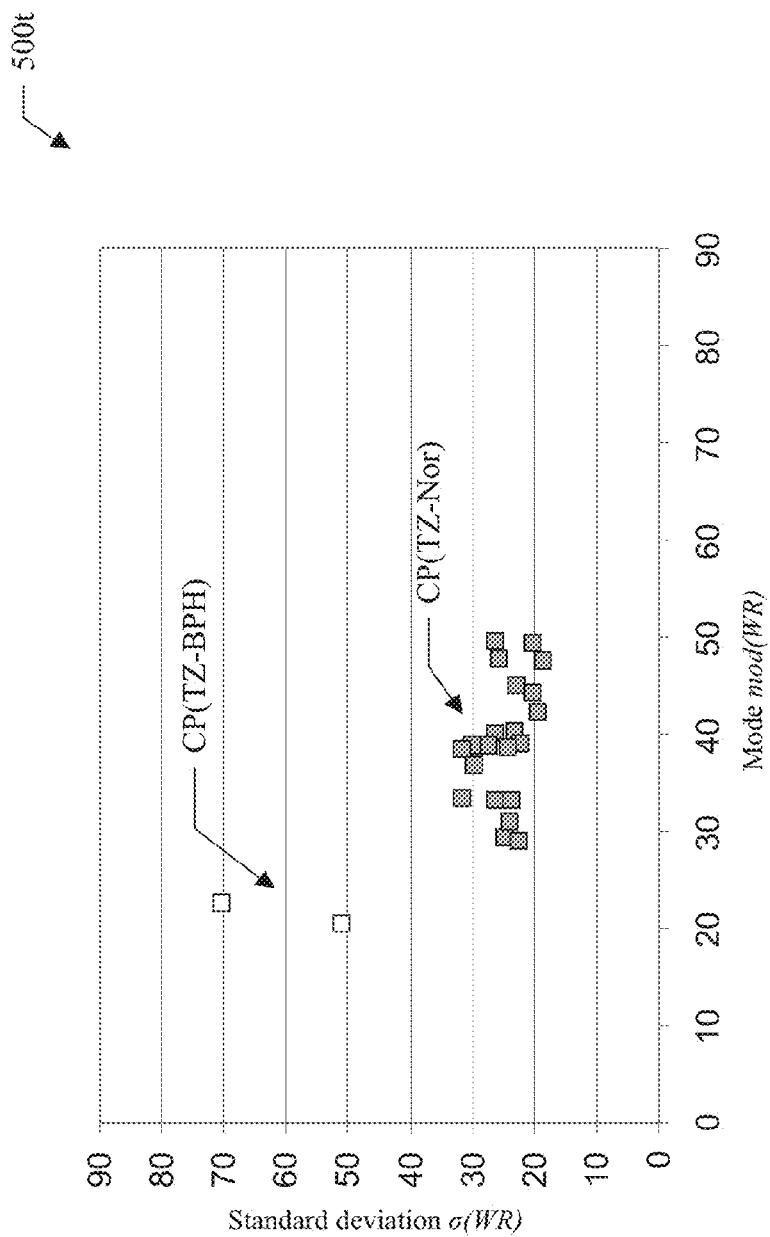

As shown in FIG. 5A for the PZ and in FIG. 5B for the TZ, the statistical parameter values mod(WR) and σ(WR) are represented in a 2D graph 500p and 500t, respectively, which plots the mode mod(WR) on the abscissa-axis and the standard deviation σ(WR) on the ordinate-axis. For this purpose, to each probability function F(WR) there is associated a combined point CP(mod(WR), σ(WR)), whose coordinates are its mode value mod(WR) for the abscissa-axis and its standard deviation value σ(WR) for the ordinate-axis.

As can be seen, the combined points CP for each category of body-parts belong to a distinct domain in the graphs 500p and 500t. Particularly, in FIG. 5A the combined points CP for the PZ are denoted with the reference CP(PZ-Nor) for normal tissue (black), with the reference CP(PZ-PCa) for PCa (dark gray), and with the reference CP(PZ-Pro) for Prostatitis (light gray); likewise, in FIG. 5B the combined points CP for the TZ are denoted with the reference CP(TZ-Nor) for normal tissue (very light gray), and with the reference CP(TZ-PBH) for BPH (white).

More formally, for each category of body-parts it is possible to calculate two mean values mean(mod) and mean(σ)—representing a center of gravity of the distribution of the mode values mod(WR) and the standard deviation values σ(WR), respectively—and two standard deviation values σ(mod) and σ(σ)—representing a dispersion of the mode values mod(WR) and the standard deviation values σ(WR) around their mean values, respectively. These values for different categories of body-parts (and particularly for different conditions in the same body-parts) are significantly different. For example, a statistically significant difference (ρ<0.01) was found for the mean values mean(mod), mean(σ) both between the PZ with normal tissue and the PZ with PCa, and between the PZ and the TZ with normal tissue, and a statistically significant difference (ρ<0.05) was found for the mean value mean(σ) between the PZ with PCa and the TZ with normal tissue (by using a one-way ANOVA analysis plus a post-hoc t-test).

Figure 5C:
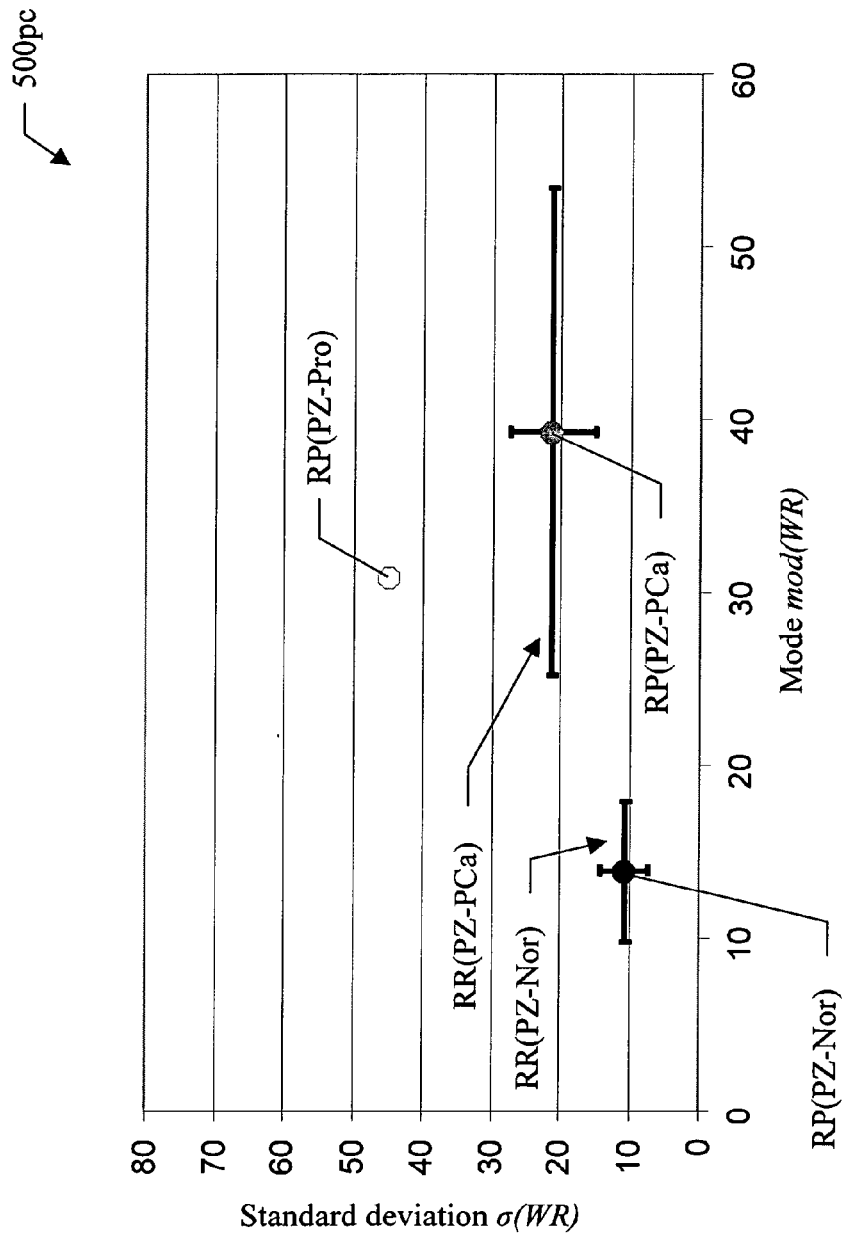
Figure 5D:
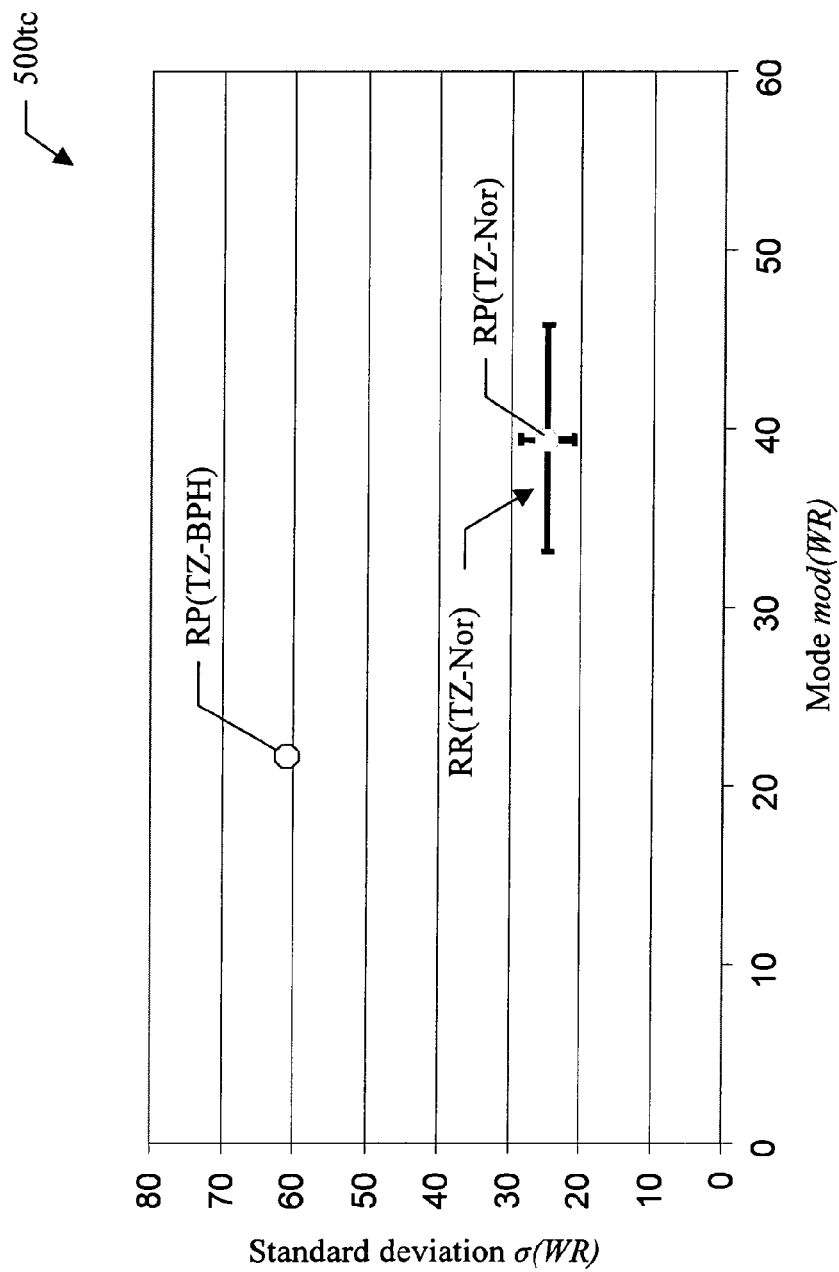

Moving to FIG. 5C and FIG. 5D, the different categories of body-parts are concentrated in another graph 500pc for the PZ and in another graph 500tc for the TZ (again plotting the mode mod(WR) on the abscissa-axis and the standard deviation σ(WR) on the ordinate-axis). For this purpose, each category of body-parts is associated with a reference point—whose coordinates are its mean value mean(mod) for the abscissa-axis and its mean value mean(σ) for the ordinate-axis—and with a reference dispersion—with an extension around the reference point equal to its standard deviation value σ(mod) along the abscissa-axis and equal to its standard deviation value σ(σ) along the ordinate-axis. Particularly, in FIG. 5C for the PZ a reference point RP(PZ-Nor) and a reference dispersion RR(PZ-Nor) are obtained for normal tissue, a reference point RP(PZ-PCa) and a reference dispersion RR(PZ-PCa) are obtained for PCa, and a reference point RP(PZ-Pro) is obtained for Prostatitis (no reference dispersion is determined in this case since only two observations are available). Likewise, in FIG. 5D for the TZ a reference point RP(TZ-Nor) and a reference dispersion RR(TZ-Nor) are obtained for normal tissue, and a reference point RP(TZ-BPH) is obtained for BPH (no reference dispersion is again determined in this case since only two observations are available).

Figure 5E:
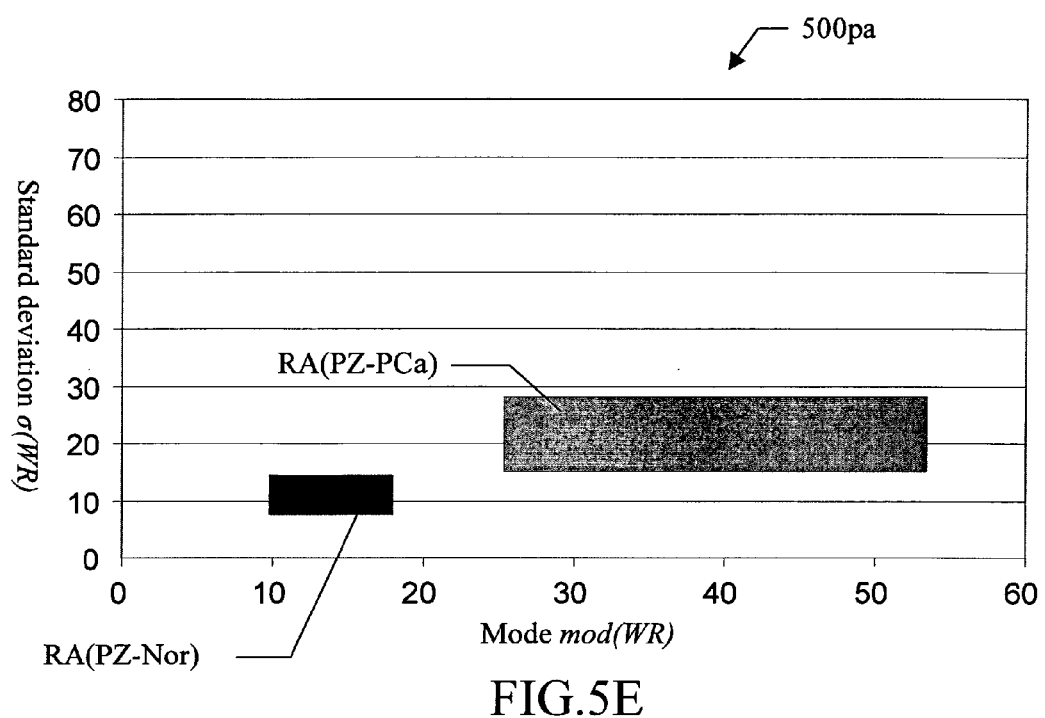

Therefore, it is possible to define a reference area for each category of body-parts; the reference area consists of a rectangle, which extends around the corresponding reference point with a size equal to the corresponding reference dispersion. Considering in particular only the PZ (which is the zone normally taken into account during the analysis of the prostate, since 80% of the cancers are found in it), in FIG. 5E there is shown a graph 500pa of its reference areas. As can be seen, a reference area RA(PZ-Nor) is defined for normal tissue and a reference area RA(PZ-PCa) is defined for PCa. This confirms that the different conditions of the PZ define well distinct domains in the graph 500pa.

Figure 6A:
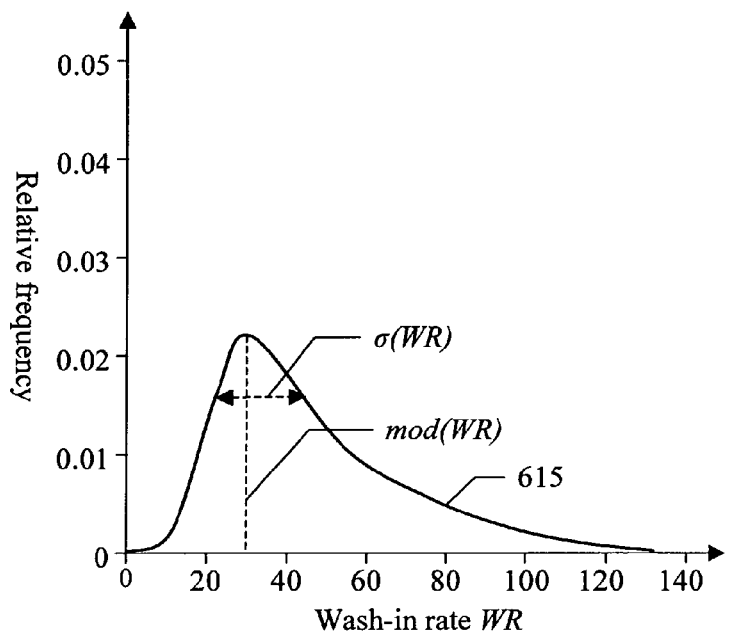
FIG. 6A-6B show an example of application of these statistical analyses according to an embodiment.

An example of application of the above-described statistical analyses according to an embodiment is shown in FIG. 6A. Particularly, whenever the prostate of a generic patient has to be analyzed, a corresponding parametric image is generated; the parametric image is then auto-scaled and normalized. A histogram obtained from a region of interest in the PZ of this parametric image is calculated, and a corresponding probability function 615 is determined. At this point, it is possible to calculate the mode value mod(WR) and the standard deviation value σ(WR) of the probability function 615.

Figure 6B:
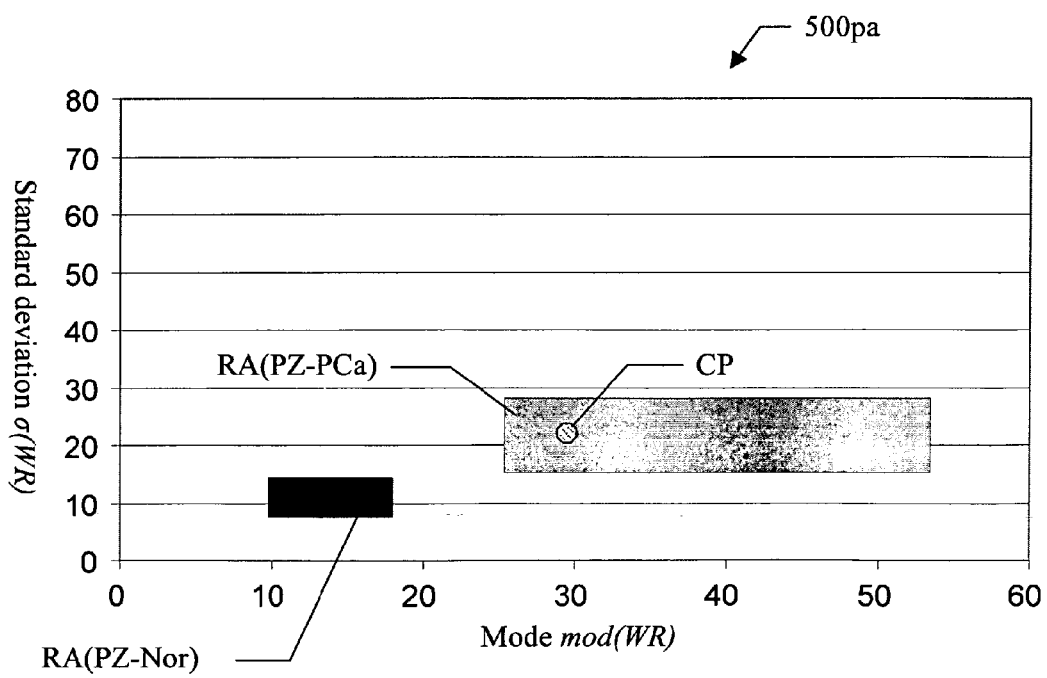

Moving to FIG. 6B, a combined point CP representing this probability function—with coordinates defined by the mode value mod(WR) and the standard deviation value σ(WR)—is then drawn on the above-defined graph 500pa (corresponding to the zone of the prostate under analysis). The position of the combined point CP with respect to the (pre-defined) reference areas RA(PZ-Nor) and RA(PZ-PCa) strongly facilitates the assessment of the condition of the prostate under analysis. Particularly, in the example at issue the combined point CP falls within the reference area RA(PZ-PCa), meaning that the prostate might be affected by a cancer (of course, with the final diagnosis that has always to be performed by a physician).

Figure 7A:
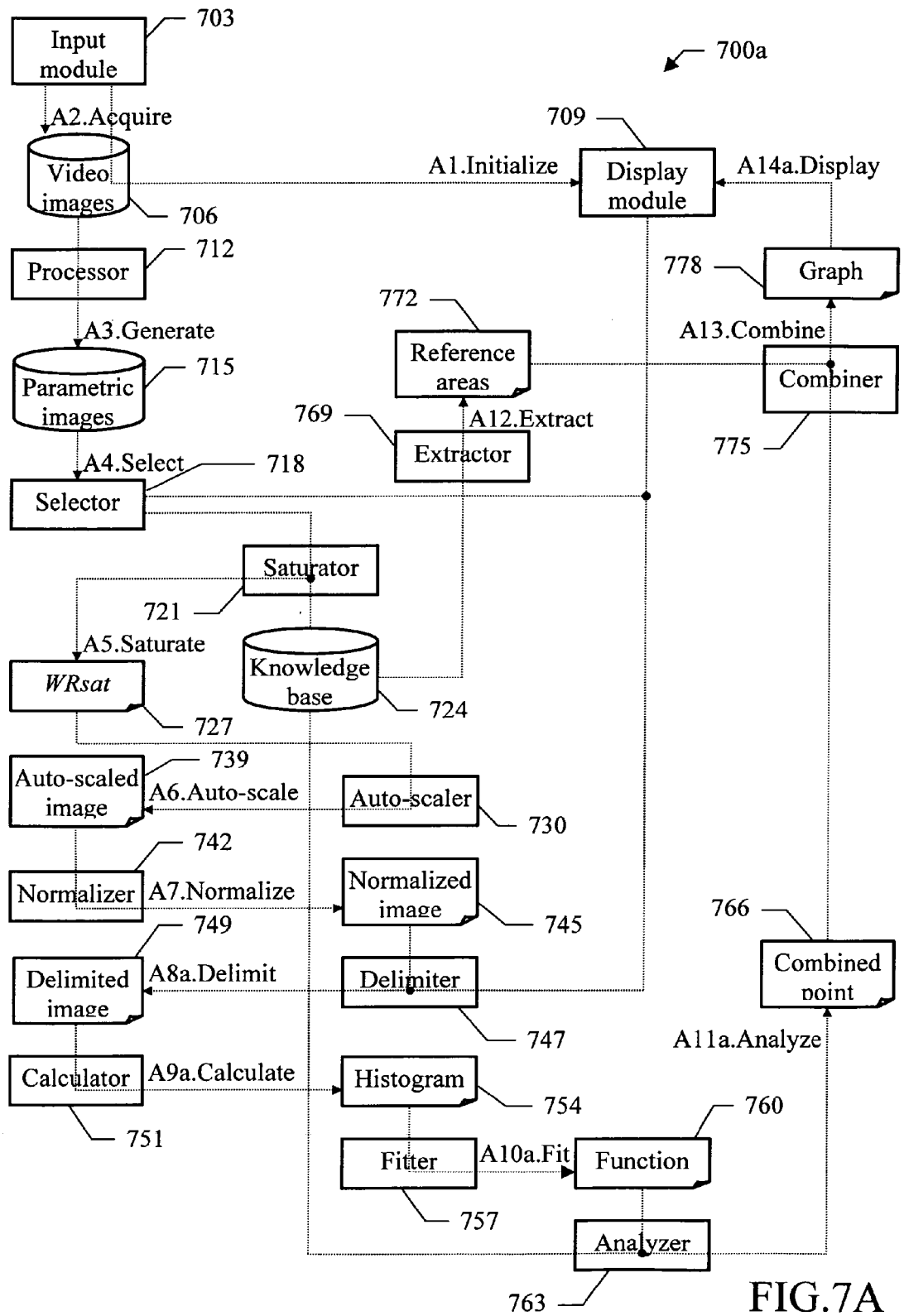
FIG. 7A shows a diagram representing the roles of the main components that may be used to implement an embodiment.

A collaboration diagram representing the main software and/or hardware components that may be used to implement the solution according to an embodiment of the invention is illustrated in FIG. 7A. These components are denoted as a whole with the reference 700a; particularly, the information (programs and data) is typically stored on the hard-disk and loaded (at least partially) into the working memory of a data-processing system (for example, the ultrasound scanner or a distinct personal computer) when the programs are running, together with an operating system and other application programs (not shown in the figure). The programs are initially installed onto the hard disk, for example, from DVD-ROM. More specifically, the figure describes the static structure of the system (by means of the corresponding components) and its dynamic behavior (by means of a series of exchanged messages, each one representing a corresponding action, denoted with sequence numbers preceded by the symbol "A").

Particularly, an input module 703 includes a driver that controls the imaging probe. For example, this imaging probe driver is provided with a transmit beam former and pulsers for generating the ultrasound pulses to be applied to the body-part under analysis; the imaging probe then receives echo waveforms that are reflected by each location of the body-part in a selected scan plane. Resulting analog RF echo signals are supplied to a receive processor, which pre-amplifies the analog RF echo signals and applies a preliminary time-gain compensation (TGC); the analog RF echo signals are then converted into digital values by an Analog-to-Digital Converter (ADC), and combined into focused beam signals through a receive beam former. The digital signals so obtained are preferably processed through further digital algorithms and other linear or non-linear signal conditioners (for example, a post-beam-forming TGC). Particularly, the receive processor applies a contrast-specific algorithm to suppress the contribution of the tissue (such as based on the above-mentioned HI, PI, PM or CPS techniques). The digital signals are then demodulated, log-compressed (in order to obtain images with well-balanced contrast), and scan-converted into a video format. This process generates a sequence of (contrast-specific) video images, which are stored into a corresponding repository 706—hereinafter, the different memory structures and their contents will be denoted with the same references for the sake of simplicity. Each video image 706 is defined by a matrix of values for respective pixels, each one corresponding to a location of the body-part. Each pixel value consists of a signal level (for example, coded on 8 bits) defining the brightness of the pixel; for example, in gray scale video images the pixel value increases from 0 (black) to 255 (white) as a function of the intensity of the corresponding echo signal (representing the acoustical response at the corresponding location of the body-part).

At the beginning of the analysis process, an operator of the scanner actuates the imaging probe and moves it around the body-part to be analyzed (before administering any contrast agent). The corresponding video images 706 are provided in succession to a display module 709 as soon as they are acquired, so as to obtain their display in real-time (action "A1.Initialize"). The operator chooses a scan plane representing the zone of the body-part to be analyzed (preferably including a suspicious region) and keeps the imaging probe in a fixed position.

The contrast agent is then administered to the patient, and the ultrasound scanner acquires a series of further video images 706 representing the perfusion process in the selected scan plane of the body-part (action "A2.Acquire"). The repository of the video images 706 is accessed by a processor 712; the processor 712 generates a corresponding sequence of parametric images, which are stored into a repository 715 (action "A3.Generate"). Each parametric image 715 is defined by a matrix of pixel values, each one representing the value of a perfusion parameter being calculated for the corresponding location of the body-part; the parametric image 715 may have either the same size as the video images 706 (when the perfusion parameter values are calculated at the pixel level) or a lower size (when a spatial sub-sampling is applied to calculate the perfusion parameter values for groups of adjacent pixels). For example, each parametric image 715 is obtained in real-time as described in the above-mentioned document EP08169794.8. In this case, for each pixel the parametric image 715 includes the wash-in rate value WR of the corresponding location of the body-part, which is calculated as soon as a peak has been detected for the corresponding pixel values in the video images 706 being available up to now (after they remained constant during the stability time-window); otherwise, the corresponding pixel value is maintained at the value 0. Preferably, the parametric image 715 is also filtered by resetting (to the value 0) each pixel value that is lower than a predefined threshold (for example, ranging from 0 to 5% of a maximum allowable pixel value in the parametric image 715), so as to disregard non-significant wash-in rate values WR (for example, due to motion artifacts).

A selector 718 is used by the operator to extract a selected parametric image from the repository 715 (action "A4.Select"); for example, this selected image 715 is the one that is obtained at the end of the analysis process (providing a summary of all the wash-in rate values WR that have been calculated over time for the body-part). A saturator 721 accesses the selected image 715 and a (pre-defined) knowledge base 724. The knowledge base 724 stores a collection of auto-scaling percentages Ps (each one being specific for a corresponding category of body-parts, or zone thereof, to be analyzed). The saturator 721 extracts the auto-scaling percentage Ps for the category of the body-part under analysis from the knowledge base 724; the saturator 721 calculates a cumulative histogram of (all) the wash-in rate values of the selected image 715, and determines a saturation value WRsat (corresponding to the wash-in rate value WR associated with the auto-scaling percentage Ps in the cumulative histogram); this saturation value WRsat is stored into a corresponding register 727 (action "A5.Saturate"). An auto-scaler 730 extracts the saturation value WRsat from the register 727; the auto-scaler 730 then generates an auto-scaled image from the selected image 715, which auto-scaled image is stored into a corresponding file 739 (action "A6.Auto-scale"); the auto-scaled image 739 is obtained from the selected image 715 by setting all the wash-in rate values WR higher than the saturation value WRsat equal to it.

A normalizer 742 accesses the auto-scaled image 739. The normalizer 742 normalizes the pixel values of the auto-scaled image 739 to a pre-defined normalization range (for example, from 0 to 1); this provides a normalized image 745, which is stored into a corresponding file (action "A7.Normalize").

A delimiter 747 retrieves the selected image 715, and displays it through the display module 709. The operator chooses a region of interest in the selected image 715 (for example, by drawing a line around it with the help of the trackball). The delimiter 747 then determines a corresponding region of interest on the normalized image 745 (for example, with the same coordinates). The delimiter 747 accordingly generates a delimited image that is stored into a corresponding file 749 (action "A8a.Delimit"); the delimitated image 749 is obtained from the normalized image 745 by resetting all the pixels outside the region of interest to the value 0.

The delimited image 749 is accessed by a calculator 751. The calculator 751 calculates a histogram of the wash-in rate values WR in the region of interest of the delimited image 749 (i.e., only for the pixel values different from 0); a representation of this histogram (for example, consisting of an array of cells, each one indicating the extension of a corresponding bin and its relative frequency) is stored into a file 754 (action "A9a.Calculate").

A fitter 757 extracts the histogram from the file 754. The fitter 757 determines a corresponding probability function F(WR) by fitting the histogram 754 with a lognormal function. A representation of this probability function F(WR) (as defined by its fitting parameters values m and s) is stored into a table 760 (action "A10a.Fit").

An analyzer 763 then extracts the fitting parameters values m,s from the table 760. The analyzer 763 calculates the values of two or more statistical parameters of the corresponding probability function F(WR) from the fitting parameters. The types of statistical parameters to be calculated (for example, the mode mod(WR) and the standard deviation σ(WR)) are extracted by the analyzer 763 from the knowledge base 724. The statistical parameters values so obtained (defining a corresponding combined point) are stored into a table 766 (action "A11a.Analyze").

Meanwhile, an extractor 769 further accesses the knowledge base 724. For each category of body-parts, or zone thereof, to be analyzed, the knowledge base 724 also stores the definition of a collection of reference areas, each one for a corresponding possible condition thereof; each reference area is defined by the corresponding values of a pair of reference parameters (for example, the reference point and the reference dispersion for the statistical parameters). For the category of the body-part under analysis (as indicated by the operator), the extractor 769 extracts the reference area definition for each possible condition thereof from the knowledge base 724, and stores these reference area definitions into a corresponding table 772 (action "A12.Extract"). A combiner 775 accesses the combined point definition 766 and the reference area definitions 772. The combiner 775 creates a 2D graph (plotting the mode mod(WR) on the abscissa-axis and the standard deviation σ(WR) on the ordinate-axis), with a representation of the combined point of the probability function F(WR) of the region of interest of the body-part under analysis (as defined by the statistical parameters values from the table 766) and a representation of the reference areas for the different possible conditions thereof (as defined by the corresponding pairs of reference parameters values from the table 772). A representation of the graph so obtained is stored into a corresponding table 778 (action "A13.Combine"). This graph 778 is then provided to the display module 709 for its display (action "A14a.Display").

Figure 7B:
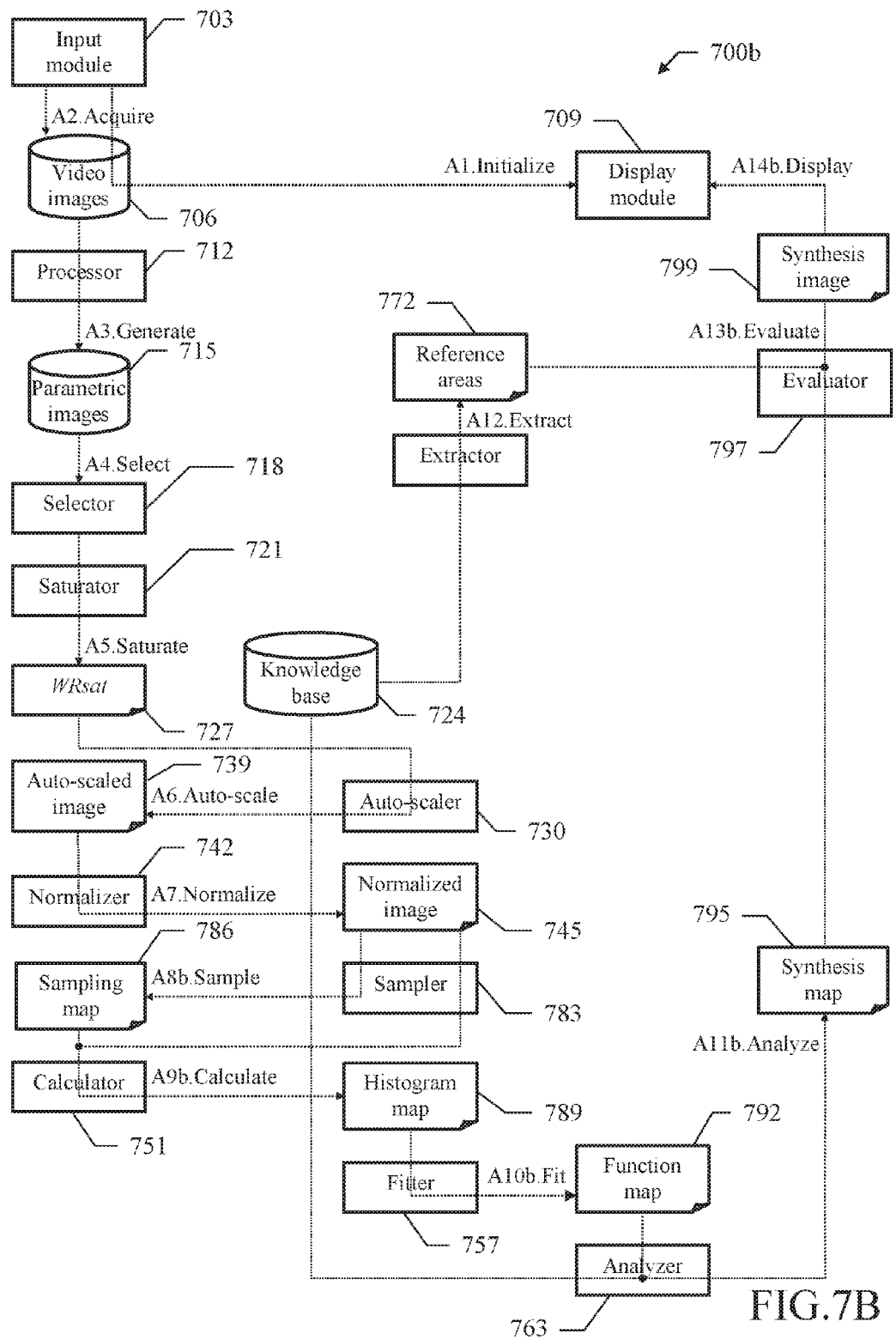
FIG. 7B shows a diagram representing the roles of the main components that may be used to implement another embodiment.

Moving to FIG. 7B, a collaboration diagram representing the main software and/or hardware components 700b that may be used to implement the solution according to another embodiment is illustrated.

As above, the normalized image 745 is generated by auto-scaling and normalizing the selected image 715. In this case, however, the normalized image 745 is accessed by a sampler 783. The sampler 783 generates a sampling map (with the same size as the normalized image 745), which is saved into a file 786 (action "A8b.Sample"). Each entry of the sampling map 786 stores the coordinates of a cell including the corresponding pixel of the normalized image 745; the cell has a predefined size (for example, 10-50×10-50 pixels), and it is centered around the corresponding pixel.

The same calculator 751 as above accesses the normalized image 745 and the sampling map 786. The calculator 751 generates a histogram map (with the same size as the sampling map 786), which is saved into a file 789 (action "A9b.Calculate"); each entry of the histogram map 789 includes the representation of the histogram of the wash-in rate values WR for its cell of the normalized image 745, as defined in the corresponding entry of the sampling map 786.

The same fitter 757 as above accesses the histogram map 789. The fitter 757 generates a function map (with the same size as the histogram map 789), which is saved into a file 792 (action "A10b.Fit"); each entry of the function map 792 includes the representation of the probability function F(WR) fitting the corresponding histogram in the histogram map 789.

The same analyzer 763 as above accesses the function map 792 (and the knowledge base 724). The analyzer 763 generates a synthesis map (with the same size as the function map 792), which is saved into a file 795 (action "A11b.Analyze"); each entry of the synthesis map 795 includes the values of the statistical parameters indicated in the knowledge base 724 (for example, again the mode mod(WR) and the standard deviation σ(WR)) that are calculated from the corresponding probability function F(WR).

As above, the extractor 769 extracts the definitions of the reference areas for the possible conditions of the category of the body-part under analysis (i.e., their pairs of reference parameters values) from the knowledge base 724, and stores them into the table 772; in this case, for each reference area the knowledge base 724 also stores the representation of a different color (for example, consisting of a corresponding index for a color lookup table), which color representations are likewise extracted from the knowledge base 724 and stored into the table 772 (same action "A12.Extract").

An evaluator 797 accesses the synthesis map 795 and the reference area definitions 772 (consisting of their pairs of reference parameters values and their color representations). The evaluator 797 then creates a synthesis image (with the same size as the synthesis map 795), which is saved into a file 799 (action "A13b.Evaluate"); for each pixel, the synthesis image 799 includes the color representation of the reference area (as defined by the corresponding pairs of reference parameters values from the table 772) wherein the corresponding combined point (as defined by the statistical parameters values from the corresponding entry of the synthesis map 796) falls—with the pixel of the synthesis image 799 that includes the representation of a different default color when the combined point does not fall within any reference area. For example, for the analysis of the PZ of the prostate it is possible to associate the color green to the reference area for normal tissue, and the color red to the reference area for PCa (with the default color equal to black). Moreover, it is also possible to overlay the synthesis image 799 on a selected video image 706 (for example, by showing the selected video image 706 in the background for the pixel values equal to black of the synthesis image 799). The synthesis image 799 is then provided to the display module 709 for its display (action "A14b.Display").

The synthesis image shows the spatial distribution of the statistical parameter values throughout the body-part, each one indicative of a corresponding characteristic of the distribution of the (auto-scaled and normalized) parameter values in a neighborhood of the corresponding location of the body-part. Particularly, the above-mentioned color representation (based on the comparison of each combined point with the reference areas) provides an overview of the whole body-part, from which it is possible to readily identify and characterize possible lesions (without the need of selecting any suspected region of interest a priori). Indeed, with reference to the above-mentioned example, a synthesis image completely colored in green (or black) indicates a healthy condition of the whole prostate, whereas a significant area of the synthesis image colored in red indicates a suspected PCa, with its size and position (of course, with the final diagnosis that has always to be performed by a physician).

Figure 8:
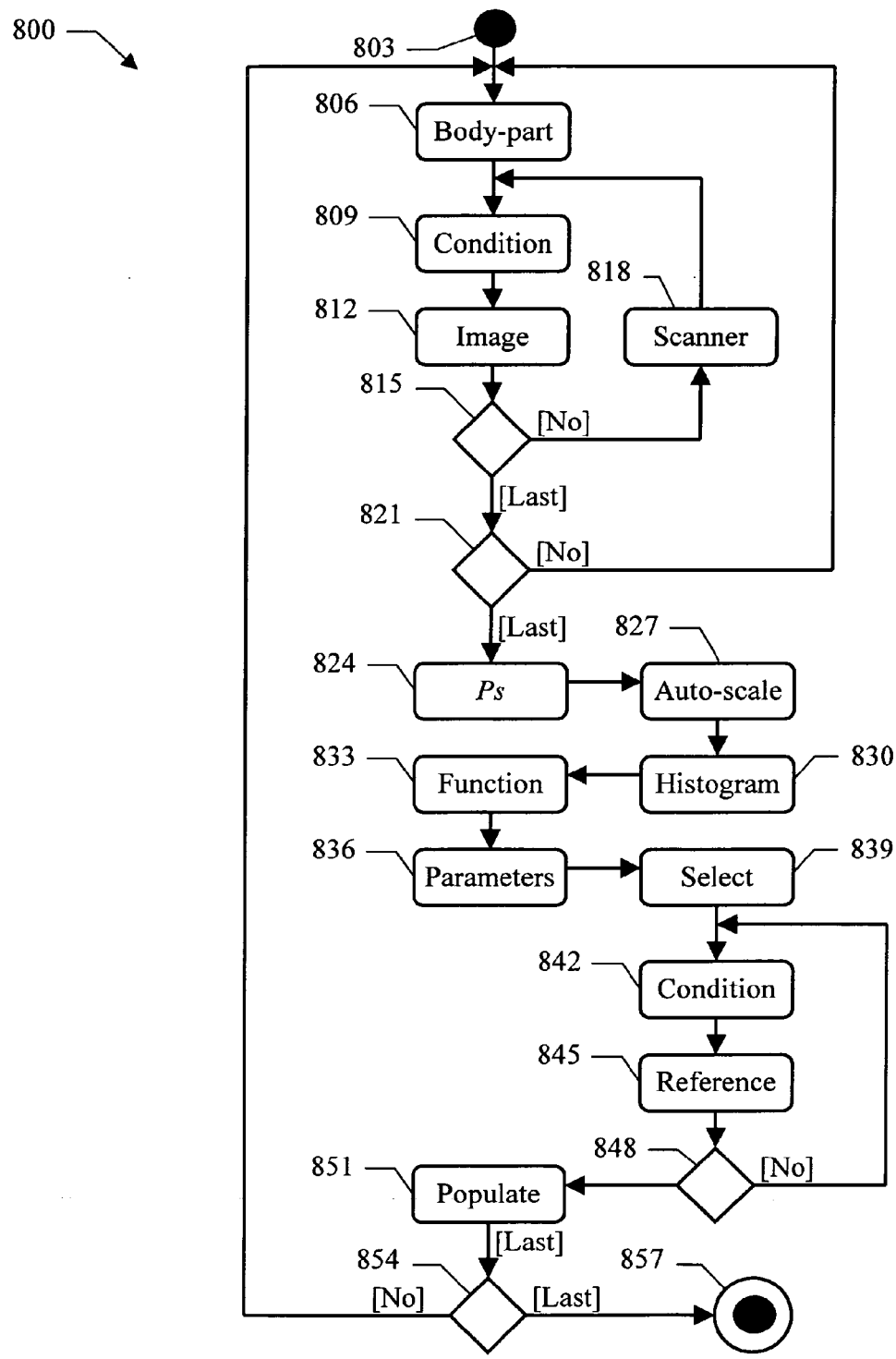
FIG. 8 is a diagram describing the flow of activities relating to a process that can be used to configure the system according to an embodiment.

Considering now FIG. 8, the flow of activities relating to a process that can be used to configure the above-described system according to an embodiment is represented with a method 800.

The method 800 begins at the black start circle 803, and then passes to block 806 wherein a category of sample body-parts, or zones thereof, is selected; the category of sample body-parts is chosen so as to provide coherent results of the above-described statistical analysis for each portion thereof in a same condition, irrespectively of its position (for example, the PZ and the TZ for the prostate).

A loop is then performed for each possible sample condition of the category of sample body-parts (for example, with normal tissue, PCa, Prostatitis and BPH). The loop begins at block 809, wherein one of the sample conditions is selected. Continuing to block 812, a parametric image of a specific sample body-part (of this category) in the sample condition is generated; this operation is performed on a sample patient, by using a sample scanner having a sample setting. A test is then made at block 815 to verify whether a sufficient number of parametric images have been acquired for the sample body-part in the sample condition (for example, 10-200). If not, the method 800 passes to block 818, wherein another sample scanner and/or another sample setting are selected. The flow of activity then returns to block 812 to generate another sample parametric image of the same category of sample body-parts in the same sample condition (on the same sample body-part or on the sample body-part of a different sample patient) with this sample scanner having this sample setting. As soon as the exit condition of the above-described loop is satisfied at block 815, the method 800 descends into block 821. In this phase, a further test is made to verify whether all the possible sample conditions of the category of sample body-parts have been processed. If not, the method 800 returns to block 809 to perform the same operations on a next sample condition of the same category of sample body-parts (on different sample patients).

Conversely, the auto-scaling percentage Ps for the category of sample body-parts is determined at block 824. The auto-scaling percentage Ps is selected so as to ensure a significant equalization (being due to the auto-scaling) of the histograms of all the sample parametric images of the category of sample body-parts (as representative of every possible parametric image that can be generated in practice). For this purpose, the auto-scaling percentage Ps should be as low as possible, and at least below the percentage of the highest wash-in rate values WR in the cumulative histogram of each sample parametric image—for example, below the percentage of its last but one bin (since otherwise no saturation at all of the wash-in rate values WR occurs). Conversely, the auto-scaling percentage Ps should be maintained as high as possible to minimize the loss of information being caused by the auto-scaling (since the saturation of the wash-in rate values WR involves a cut of a corresponding tail of the histograms). The auto-scaling percentage Ps is then selected as a trade-off between these opposed requirements; for example, the auto-scaling percentage Ps is set to the highest percentage of the last but one bin in the cumulative histograms of all the sample parametric images, being reduced by a predefined value (for example, 0-5%).

Proceeding to block 827, each sample parametric image is auto-scaled (by using the auto-scaling percentage Ps so determined). A histogram of each (auto-scaled) sample parametric image is then calculated at block 830. The method continues to block 833, wherein a sample probability function F(WR) is determined by curve fitting from each sample histogram. With reference now to block 836, the values of a set of sample statistical parameters is calculated for each sample probability function (for example, the mean mean(WR), the mode mod(WR), the median med(WR), the standard deviation σ(WR), and the skewness γ(WR)). Continuing to block 839, two (or more) statistical parameters to be used for the statistical analysis of the category of sample body-parts are determined among the sample statistical parameters or any combinations thereof; these statistical parameters are chosen as the ones that maximize the ability to identify the different sample conditions of the category of sample body-parts—for example, by means of a Principle Component Analysis.

A loop is then performed for each sample condition of the category of sample body-parts. The loop begins at block 842, wherein one of the sample conditions is selected. Continuing to block 845, the mean and the standard deviation of the values of each statistical parameter so determined from the sample probability functions for this sample condition are calculated, so as to define the corresponding reference area. A test is then made at block 848 to verify whether all the sample conditions of the category of sample body-parts have been processed. If not, the method 800 returns to block 842 to perform the same operations on a next sample condition of the same category of sample body-parts.

Conversely, the flow of activity descends into block 851; in this phase, the information so obtained for the category of sample body-parts (i.e., the auto-scaling percentage Ps) and for its sample conditions (i.e., the definition of the corresponding reference areas) is used to populate the knowledge base of the proposed system. A test is then made at block 854 to verify whether another category of sample body-parts is to be processed. If so, the flow of activity returns to block 806 to perform the same operations on a next category of sample body-parts. Conversely, the method 800 ends at the concentric white/black stop circles 857.

Modifications

Naturally, in order to satisfy local and specific requirements, a person skilled in the art may apply to embodiments described above many logical and/or physical modifications and alterations. More specifically, although embodiments have been described with a certain degree of particularity, it should be understood that various omissions, substitutions and changes in the form and details as well as other embodiments are possible. Particularly, one or more embodiments may even be practiced without the specific details (such as the numerical examples) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment may be incorporated in any other embodiment as a matter of general design choice.

Particularly, an embodiment lends itself to be put into practice with an equivalent method (by using similar steps, removing some steps being non-essential, or adding further optional steps); moreover, the steps may be performed in a different order, concurrently or in an interleaved way (at least in part).

It should be noted that an embodiment of a method may be implemented independently of any interaction with the patient (and particularly with the contrast agent that may be pre-administered thereto before performing the method). Moreover, the contrast agent may also be administered to the patient in a non-invasive manner, or in any case without any substantial physical intervention thereon that would require professional medical expertise or entail any health risk for the patient (for example, intramuscularly or orally). Although an embodiment facilitates the task of a physician, it generally only provides intermediate results that may help him/her in examining the body-part—for example, for diagnostic purposes (even though the diagnosis for curative purposes stricto sensu is always made by the physician himself/herself).

Similar considerations apply if each parametric image is based on another perfusion parameter (for example, a blood volume, a mean velocity, a maximum intensity, a time-to-peak, a wash-in time, a time-of-arrival, a square-root of the peak value divided by the square of the wash-in duration, or any combination thereof). Moreover, the parametric images may be generated in any other way—for example, off-line by fitting the echo signals that have been recorded during the whole perfusion process for each pixel with a mathematical model function (even at the level of groups of pixels instead of single pixels). Moreover, nothing prevents applying an embodiment to 3-D parametric images. More generally, the parametric image and the auto-scaled image may be replaced by equivalent maps, each one including whatever parameter values (as originally calculated and auto-scaled, respectively) that characterize corresponding locations of the body-part; the parameter values may also be not in a video format (since these maps do not necessarily have to be displayed).

An embodiment lends itself to be put into practice by calculating (and displaying in any way—for example, on the monitor or on a print-out) whatever statistical indicator, or combination of statistical indicators, of the distribution of the auto-scaled parameter values in the region of interest; for example, it is possible to provide only their histogram, the corresponding probability function, and/or the value of any other statistical parameter (for example, its skewness). In addition, it is also possible to display the auto-scaled parametric images; the auto-scaled parametric images may also be overlaid on a selected filtered image in the background, on the (original) video images outside a region of interest, or even combined with non contrast-specific images (such as fundamental B-mode images being obtained from the echo signals directly).

An embodiment lends itself to be put into practice with equivalent contrast agents. In any case, there is not excluded the possibility of applying an embodiment to any other medical imaging system—for example, based on Magnetic Resonance Imaging (MRI) or X-ray Computed Tomography (CT), even without the administration of any contrast agent.

Nothing prevents applying a method embodiment a reverse logic. In this case, the auto-scaling percentage Ps is referred to the value 0% (for example, ranging from 0.01% to 20%); therefore, once determined the saturation value WRsat as above, the parametric image is auto-scaled by setting its wash-in rate values WR lower than the saturation value WRsat equal to it.

Likewise, the saturation value WRsat may be determined in any other equivalent way, even without calculating any cumulative histogram. For example, the same result may be achieved by arranging the pixel values in decreasing order and scanning them until reaching the complement of the auto-scaling percentage (100%-Ps), or more generally with any other algorithm suitable to partition an ordered sequence of the wash-in rate values WR into two subsets—each one consisting of an (integer) number of wash-in rate values WR corresponding (for example, being closest to) a predefined percentage of the wash-in rate values WR; for example, it is possible to determine the saturation value WRsat to have the wash-in rate values WR lower than (or equal) to it in the auto-scaling percentage Ps.

The proposed values of the auto-scaling percentage Ps are merely illustrative, and they must not be interpreted in a limitative manner; for example, it is possible to use different values of the auto-scaling percentage Ps, or conversely the same value for all the body-parts.

The auto-scaled parametric images may be normalized in any other way to whatever normalization range (even if this operation is not strictly necessary—for example, when the statistical analysis is only based on shape indicators of the corresponding probability function).

Similar considerations apply if each histogram has a different structure (for example, with a different number, and then width, of the bins).

Alternatively, each probability function may be determined with equivalent techniques—even without making any assumption about its nature (for example, by means of neural networks). Likewise, it is possible to determine the probability function by fitting the corresponding histogram with any other function—for example, a gamma-variate function, a local density random walk function, and the like.

Naturally, the proposed statistical parameters are merely illustrative and they should not be interpreted in a limitative manner. More generally, it is possible to use any number of statistical parameters or combinations thereof (down to a single one).

In addition, the statistical parameter values may also be obtained directly from the auto-scaled values, even without calculating the corresponding histogram and/or probability function.

Nothing prevents applying the auto-scaling and/or the statistical analysis to different sets of the parameter values; for example, it is possible to apply the auto-scaling only to the region of interest, or conversely to apply the statistical analysis to the whole body-part. Moreover, the region of interest may also be selected on any other image of the body-part (for example, the auto-scaled image itself, one of the original video images, or one of the filtered images).

In any case, the statistical parameter values may be displayed in any other way (even with a simple table). On the other hand, graphs with 3 or more dimensions may be exploited (for example, with 3 axes and a further dimension defined by a colorization for representing a combined point being defined by 4 statistical parameters).

Similar considerations apply to the reference areas. For example, they may be defined by different reference parameters (for example, around the mean value mean(mod), mean ($\sigma$) and/or with different shapes (for example, in a range around their center being defined by a radius equal to a predefined multiple of the standard deviation value $\sigma$(mod), $\sigma(\sigma)$). In any case, this feature may be omitted in a basic implementation of an embodiment.

In any case, it is emphasized that an embodiment based on the use of multiple statistical parameter values (and their display in the corresponding graph) is suitable to be used even without the proposed auto-scaling of the parametric image (i.e., by calculating them on the original parametric image directly).

The synthesis image may be displayed in any way (for example, on the monitor or on a print-out); moreover, it is possible to overlay the synthesis image on a selected filtered image or contrast-specific image, or to display it alone (without any other image in the background).

The cell being used to calculate the statistical parameter values of each pixel in the synthesis image may have any other size (sufficiently large to provide statistically significant results, even changing throughout the (normalized) auto-scaled image) and/or shape (for example, circle-like). Moreover, the possibility of simply partitioning the auto-scaled parametric image into fixed cells, so as to obtain a synthesis image with the same statistical parameter values for all the pixels of each cell (with a chessboard effect), is not excluded.

Nothing prevents creating the synthesis image for a region of interest only of the (normalized) auto-scaled image.

More generally, each pixel of the synthesis image may represent any value based on the corresponding statistical parameter values. For example, in an alternative embodiment, it is possible to set each pixel of the synthesis image simply to the corresponding statistical parameter values. Particularly, when the value of a single statistical parameter is calculated for each pixel (for example, the skewness), it may be represented with different colors, for example, brighter as the statistical parameter values increase; alternatively, when the values of two statistical parameters are calculated for each pixel (for example, as above the mode and the standard deviation), they may be represented with different colors for the mode value and by different brightness (of the color representing the corresponding mode value) for the standard deviation value.

Moreover, it is possible to set each pixel of the synthesis image in a different way (according to the comparison between its combined point and the available reference areas); for example, the pixel may be set to colors that change gradually as the combined point moves between the different reference areas.

In any case, it is emphasized that an embodiment for creating the synthesis image is suitable to be used even without the proposed auto-scaling of the parametric image (i.e., by operating on the original parametric image directly).

An embodiment may be configured in any other way. For example, the auto-scaling percentage Ps of each body part (or zone thereof) may be set to different values based on the sample parametric images; alternatively, it is also possible to determine the optimal value of the auto-scaling percentage Ps with simulation techniques, or conversely to use a same predefined auto-scaling percentage Ps for all the body-parts.

Any other procedure is suitable for populating the knowledge base of the proposed system. For example, it is possible to implement an autonomic system, wherein the knowledge base is continuously updated during its use (according to input provided by the physicians using the corresponding system).

Alternatively, the statistical parameters to be used for the statistical analysis of the probability functions may be determined with other techniques, or they may be predefined (even of the same type for all the body-parts).

An embodiment may be implemented as a plug-in for a pre-existing control program of the ultrasound scanner, directly in the same control program, or as a stand-alone application (even running on a distinct computer or provided as a network service). Similar considerations apply if the program (which may be used to implement each embodiment) is structured in a different way, or if additional modules or functions are provided; likewise, the memory structures may be of other types, or may be replaced with equivalent entities (not necessarily consisting of physical storage media). In any case, the program may take any form suitable to be used by any data-processing system or in connection therewith (for example, within a virtual machine); particularly, the program may be in the form of external or resident software, firmware, or microcode (either in object code or in source code—for example, to be compiled or interpreted). Moreover, it is possible to provide the program on any computer-usable medium; the medium can be any element suitable to contain, store, communicate, propagate, or transfer the program. For example, the medium may be of the electronic, magnetic, optical, electromagnetic, infrared, or semiconductor type; examples of such medium are fixed disks (where the program can be pre-loaded), removable disks, tapes, cards, wires, fibers, wireless connections, networks, electromagnetic waves, and the like. In any case, an embodiment lends itself to be implemented even with a hardware structure (for example, integrated in a chip of semiconductor material), or with a combination of software and hardware.

Similar considerations apply if the ultrasound scanner has a different structure or includes other units (for example, with an imaging probe of the linear-, convex-, phased-, or matrix-array type). Alternatively, an embodiment is applied in a diagnostic system that consists of an ultrasound scanner and a distinct computer (or any equivalent data-processing system); in this case, the recorded information is transferred from the ultrasound scanner to the computer for its processing (for example, through a digital, analogue or network connection).

The above-described embodiments, as well as any modification thereof, can be used in a conventional diagnostic method (which includes the above-described steps of administering the contrast agent, acquiring the required data from the body-part under analysis, and processing them as described-above so as to obtain information that may allow evaluating the condition of the body-part). Particularly, the contrast agent may be injected in an intra-arterial, intralymphatic, subcutaneous, intramuscular, intradermal, intraperitoneal, interstitial, intrathecal or intratumoral way, as a continuous infusion (with or without the application of destructive flashes), orally (for example, for imaging the gastro-intestinal tract), via a nebulizer into the airways, and the like. Moreover, even though in the preceding description reference has been made to the analysis of the prostate, this is not to be intended in a limitative manner—with an embodiment that may likewise find application in any kind of analysis of other body-parts (for example, in liver, breast, and so on). More generally, the term diagnostic method should be interpreted in its broadest meaning (for example, to identify and/or characterize pathological conditions in the region of interest, to monitor the evolution of a pathological condition or the response to a treatment, and the like).

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

The invention claimed is:

1. A data-processing method for analyzing a body-part, the method including the steps of:
   providing a parametric map including a plurality of parameter values each one characterizing a corresponding location of the body-part,
   determining a saturation value partitioning an ordered sequence of processing parameter values, corresponding to processing locations into a first subset and a second subset consisting of a number of the processing parameter values being determined according to a predefined auto-scaling percentage,
   generating an auto-scaled map including, for each processing location, an auto-scaled value being equal to:
   a) the corresponding processing parameter value if included in the second subset, or
   b) the saturation value if the corresponding processing parameter value is included in the first subset,
   determining at least one statistical indicator of at least one distribution of a plurality of the auto-scaled values corresponding to analysis locations included in the processing locations, and displaying a representation of said at least one statistical indicator to provide an indication of a condition of an analysis region of the body-part defined by the analysis locations.

2. The method according to claim 1, wherein each parameter value is indicative of a perfusion of the corresponding location of the body-part being perfused with a pre-administered contrast agent.

3. The method according to claim 1, wherein the processing parameter values of the first subset are higher than or equal to the saturation value.

4. The method according to claim 1, wherein the step of determining a saturation value includes:
   calculating a cumulative histogram of the processing parameter values, and
   setting the saturation value to a processing parameter value associated with the auto-scaling percentage in the cumulative histogram.

5. The method according to claim 1, wherein the auto-scaling percentage ranges from 80% to 99.99%.

6. The method according to claim 1, wherein the step of determining at least one statistical indicator further includes:
   normalizing the auto-scaled values to a predefined normalization range.

7. The method according to claim 1, wherein the step of determining at least one statistical indicator includes:
   calculating a histogram of the auto-scaled values corresponding to the analysis locations.

8. The method according to claim 7, wherein the step of determining at least one statistical indicator further includes:
   calculating a probability function of the histogram by fitting the histogram with a parametric function.

9. The method according to claim 8, wherein the step of determining at least one statistical indicator includes: calculating a value of at least one statistical parameter of the probability function.

10. The method according to claim 9, wherein the at least one statistical parameter is a plurality of statistical parameters, the method further including the step of:
    displaying an indication of the respective values of the statistical parameters in a graph having a visualization dimension for each statistical parameter.

11. The method according to claim 10, wherein a knowledge base is provided for storing an indication of at least one set of respective reference ranges for the statistical parameters, each set of reference ranges being indicative of a corresponding estimated condition of the body-part, the method further including the steps of:
    retrieving the at least one set of reference ranges from the knowledge base, and
    displaying a representation of the at least one set of reference ranges in the graph.

12. The method according to claim 1, wherein the step of determining at least one statistical indicator includes:
    calculating a value of at least one statistical parameter of the distribution of the auto-scaled values corresponding to the analysis locations.

13. The method according to claim 1, wherein the processing locations consist of all the locations of the parametric map, and the analysis locations consist of a subset of the locations of the parametric map.

14. The method according to claim 1, wherein the at least one distribution of the auto-scaled values corresponding to the analysis locations consists of a plurality of distributions of the auto-scaled values corresponding to the analysis locations each one for a synthesis location, the analysis locations of each synthesis location consisting of a subset of the locations including the synthesis location, and wherein the method further includes the step of:
    creating a synthesis image, for each synthesis location the synthesis image including a synthesis value being based on the corresponding at least one statistical indicator.

15. The method according to claim 14, wherein the analysis locations of each synthesis location consist of a pre-defined common number of locations being centered around the synthesis location.

16. The method according to claim 14, wherein the at least one statistical indicator of each synthesis location is a respective value of a plurality of statistical parameters of the corresponding distribution of the auto-scaled values, and wherein a knowledge base is provided for storing an indication of at least one set of respective reference ranges for the statistical parameters, each set of reference ranges being indicative of a corresponding estimated condition of the body-part, the step of creating a synthesis image including:
    retrieving the at least one set of reference ranges from the knowledge base, and
    setting the synthesis value of each synthesis location according to a comparison between the values of the statistical parameters of the synthesis location and the at least one set of reference ranges.

17. The method according to claim 16, wherein the knowledge base is further adapted to store an indication of at least one reference value, each reference value for a corresponding set of reference ranges, the step of creating a synthesis image including:
    retrieving the at least one reference value from the knowledge base, and
    setting the synthesis value of each synthesis location to the reference value of the set of reference ranges including the values of the respective statistical parameters of the synthesis location, or to a default value otherwise.

18. The method according to claim 14, wherein the synthesis locations consists of all the analysis locations.

19. A computer program product including a non-transitory computer readable medium embodying a computer program, the computer program including code means directly loadable into a working memory of a data-processing system thereby configuring the data-processing system to perform the data-processing method according to claim 1.

20. A diagnostic system including:
    a microprocessor configured for:
    providing a parametric map including a plurality of parameter values each one characterizing a corresponding location of the body-part,
    determining a saturation value partitioning an ordered sequence of processing parameter values, corresponding to processing locations into a first subset and a second subset consisting of a number of the processing parameter values being determined according to a pre-defined auto-scaling percentage,
    generating an auto-scaled map including, for each processing location, an auto-scaled value being equal to:
       a) the corresponding processing parameter value if included in the second subset, or
       b) the saturation value if the corresponding processing parameter value is included in the first subset,
    determining at least one statistical indicator of at least one distribution of a plurality of the auto-scaled values corresponding to analysis locations included in the processing locations, and
    configured for displaying a representation of said at least one statistical indicator on a monitor or on a print-out to provide an indication of a condition of an analysis region of the body-part defined by the analysis locations.

21. A configuration method for configuring a diagnostic system, comprising:
providing a parametric map including a plurality of parameter values each one characterizing a corresponding location of the body-part,
determining a saturation value partitioning an ordered sequence of processing parameter values, corresponding to processing locations into a first subset and a second subset consisting of a number of the processing parameter values being determined according to a predefined auto-scaling percentage,
generating an auto-scaled map including, for each processing location, an auto-scaled value being equal to:
a) the corresponding processing parameter value if included in the second subset, or
b) the saturation value if the corresponding processing parameter value is included in the first subset,
determining at least one statistical indicator of at least one distribution of a plurality of the auto-scaled values corresponding to analysis locations included in the processing locations,
wherein the configuration method includes the steps of:
providing a plurality of sample parametric maps being acquired with different scanners and/or settings thereof, each sample parametric map including a plurality of sample parameter values each one characterizing a corresponding sample location of a sample body-part corresponding to said body-part, and
determining the auto-scaling percentage according to the sample parametric maps.

22. A computer program product including a non-transitory computer readable medium embodying a computer program, the computer program including code means directly loadable into a working memory of a data-processing system thereby configuring the data-processing system to perform the configuration method according to claim 21.

23. A configuration method for configuring a diagnostic system including:
providing a parametric map including a plurality of parameter values each one characterizing a corresponding location of the body-part,
determining a saturation value partitioning an ordered sequence of processing parameter values, corresponding to processing locations into a first subset and a second subset consisting of a number of the processing parameter values being determined according to a predefined auto-scaling percentage,
generating an auto-scaled map including, for each processing location, an auto-scaled value being equal to:
a) the corresponding processing parameter value if included in the second subset, or
b) the saturation value if the corresponding processing parameter value is included in the first subset,
determining a plurality of statistical parameters from the auto-scaled values corresponding to the analysis locations included in the processing locations,
displaying an indication of the respective values of the statistical parameters in a graph having a visualization dimension for each statistical parameter,
providing a knowledge base storing an indication of at least one set of respective reference ranges for the statistical parameters, each set of reference ranges being indicative of a corresponding estimated condition of the body-part,
retrieving the at least one set of reference ranges from the knowledge base, and
displaying a representation of the at least one set of reference ranges in the graph,
the method including the steps of:
providing a plurality of sample parametric maps being acquired with different scanners and/or settings thereof, each sample parametric map including a plurality of sample parameter values each one characterizing a corresponding sample location of a sample body-part corresponding to said body-part, wherein the sample parametric maps include a plurality of subsets of the sample parametric maps each one for a different estimated condition of the sample body-part,
determining the auto-scaling percentage according to the sample parametric maps;
determining a sample saturation value for each sample parametric map, the sample saturation value partitioning an ordered sequence of the sample parameter values of the sample parametric map into a first sample subset and a second sample subset consisting of a number of the sample parameter values being determined according to the auto-scaling percentage,
generating a plurality of sample auto-scaled maps each one of the plurality of sample auto-scaled maps generated from a corresponding sample parametric map, each one of the plurality of sample auto-scaled maps including, for each sample location of the sample body-part, a sample auto-scaled value being equal to:
a) the corresponding sample parameter value of the sample parametric map if included in the second sample subset, or
b) the sample saturation value if the corresponding sample parameter value of the sample parametric map is included in the first subset,
calculating a plurality of sample statistical parameter values of the distribution of the sample auto-scaled values of each sample auto-scaled map, and
calculating the set of reference ranges of each estimated condition from the sample statistical parameter values of the corresponding subset of sample parametric maps.

24. The method according to claim 23, further including the step of:
selecting the statistical parameters from the sample statistical parameters or combinations thereof to optimize a differentiation of the estimated conditions.

25. A diagnostic method for analyzing a body-part of a patient, the diagnostic method including the steps of:
administering a contrast agent to the patient,
applying an interrogation signal to the body-part,
acquiring a sequence of input maps each one including a plurality of input values each one indicative of a response to the interrogating signal of a corresponding location of the body-part, wherein a parametric function is associated with the sequence of input values of each location, a parametric map including a plurality of parameter values each one characterizing a corresponding location of the body-part is calculated by setting each parameter value according to the corresponding parametric function, and the parametric map is processed by:
determining a saturation value partitioning an ordered sequence of processing parameter values, corresponding to processing locations into a first subset and a second subset consisting of a number of the processing parameter values being determined according to a predefined auto-scaling percentage,
generating an auto-scaled map including, for each processing location, an auto-scaled value being equal to:

a) the corresponding processing parameter value if included in the second subset, or
b) the saturation value if the corresponding processing parameter value is included in the first subset, determining at least one statistical indicator of at least one distribution of a plurality of the auto-scaled values corresponding to selected analysis locations included in the processing locations, displaying a representation of said at least one statistical indicator, and evaluating a condition of an analysis region of the body-part defined by the analysis locations according to the representation of said at least one statistical indicator.

* * * * *